United States Patent
Kato et al.

[11] Patent Number: 6,045,673
[45] Date of Patent: Apr. 4, 2000

[54] GAS SENSOR

[75] Inventors: Nobuhide Kato, Ama-gun; Kunihiko Nakagaki, Nagoya, both of Japan

[73] Assignee: NGK Insulators, Ltd., Japan

[21] Appl. No.: 08/927,639

[22] Filed: Sep. 11, 1997

[30] Foreign Application Priority Data

Sep. 19, 1996 [JP] Japan ................................ 8-247754

[51] Int. Cl.[7] .............................................. G01N 27/407
[52] U.S. Cl. ........................ 204/425; 204/426; 204/427;
205/781; 205/784; 205/784.5; 205/785;
205/786.5; 205/788
[58] Field of Search .................................. 204/421–429;
205/781, 784, 784.5, 785, 786.5, 788

[56] References Cited

U.S. PATENT DOCUMENTS

| | | | |
|---|---|---|---|
| 4,645,572 | 2/1987 | Nishizawa et al. | 204/1 T |
| 4,668,374 | 5/1987 | Bhagat et al. | 204/412 |
| 4,824,549 | 4/1989 | Hamada et al. | 204/410 |
| 5,145,566 | 9/1992 | Logothetis et al. | 204/153.18 |
| 5,476,001 | 12/1995 | Hoetzel et al. | 73/23.31 |
| 5,763,763 | 6/1998 | Kato et al. | 205/781 |
| 5,772,965 | 6/1998 | Kato et al. | 204/427 |

FOREIGN PATENT DOCUMENTS

| | | |
|---|---|---|
| 0 678 740 A1 | 10/1995 | European Pat. Off. . |
| 0 731 351 A2 | 9/1996 | European Pat. Off. . |
| 0 731 351 A3 | 4/1997 | European Pat. Off. . |
| 0 769 693 A1 | 4/1997 | European Pat. Off. . |
| 0 791 828 A1 | 8/1997 | European Pat. Off. . |
| 63-38154 | 2/1988 | Japan . |
| 64-39545 | 2/1989 | Japan . |
| 1-277751 | 11/1989 | Japan . |
| 2-1543 | 1/1990 | Japan . |
| 8-271476 | 10/1996 | Japan . |
| WO 95/30146 | 11/1995 | WIPO . |

*Primary Examiner*—T. Tung
*Attorney, Agent, or Firm*—Parkhurst & Wendel, L.L.P.

[57] ABSTRACT

Disclosed is a gas sensor comprising a first internal space for making communication with the external space via a first diffusion rate-determining section, a first electrochemical pumping cell for controlling the oxygen concentration in the atmosphere in the first internal space to have a predetermined value, a second internal space for making communication with the first internal space via a second diffusion rate-determining section, a second electrochemical pumping cell for finely adjusting the oxygen concentration in the atmosphere in the second internal space to have a predetermined value, a third internal space for making communication with the second internal space via a third diffusion rate-determining section, a third electrochemical pumping cell for pumping out oxygen produced by reduction or decomposition of a component having bound oxygen in the measurement gas in the third internal space, and an ammeter Ip for detecting a pumping current which is allowed to flow in accordance with the pumping operation effected by the third electrochemical pumping cell. Accordingly, it is possible to avoid interference exerted on the sensitivity for NO by the change in oxygen concentration in exhaust gas, and improve the measurement accuracy for the measurement gas component.

10 Claims, 10 Drawing Sheets

NOx CONCENTRATION (ppm)
<MEASUREMENT CONDITION>
BASE GAS: $N_2$-NO-$O_2$-$H_2O$ SYSTEM, $O_2$ = 5 %, $H_2O$ = 5 %
GAS FLOW AMOUNT: 500 cc/min
DEVICE TEMPERATURE: 700 °C $O_2$ CONCENTRATION (%)
<MEASUREMENT CONDITION>
BASE GAS: $N_2$-NO-$O_2$-$H_2O$ SYSTEM, NO = 300 ppm, $H_2O$ = 5 %
GAS FLOW AMOUNT: 500 cc/min
DEVICE TEMPERATURE: 700 °C

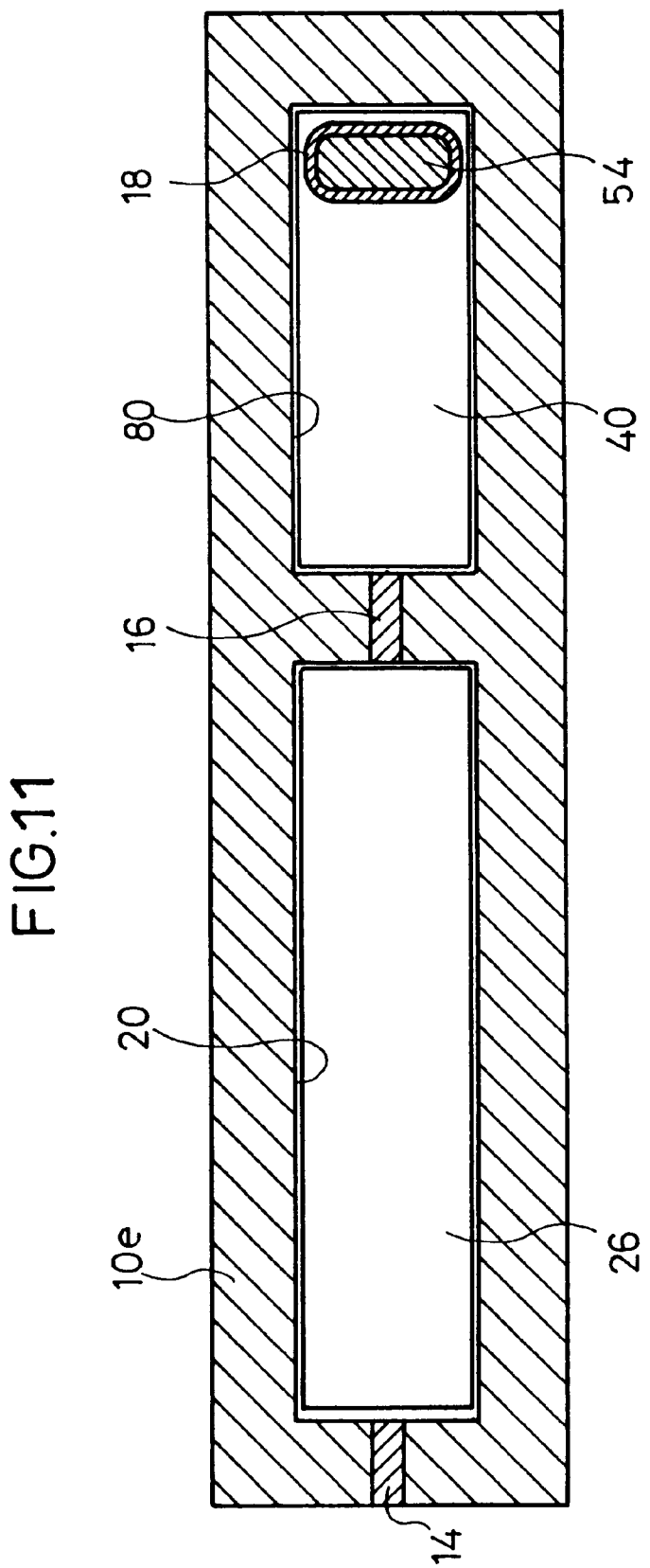

GAS SENSOR

BACKGROUND OF THE INVENTION

1. Field of the Invention

The present invention relates to a gas sensor for measuring oxides such as NO, $NO_2$, $SO_2$, $CO_2$, and $H_2O$, and inflammable gases such as CO and CnHm contained, for example, in atmospheric air and exhaust gas discharged from vehicles or automobiles.

2. Description of the Related Art

Various measuring systems and apparatuses have been hitherto suggested in order to know the concentration of a desired gas component contained in a measurement gas.

Those known as methods for measuring NOx in a measurement gas such as combustion gas include, for example, a technique based on the use of the NOx-reducing ability of Rh, in which a sensor comprising a Pt electrode and an Rh electrode formed on an oxygen ion-conductive solid electrolyte such as zirconia is used to measure an electromotive force generated between the both electrodes.

The sensor as described above involves problems in that the electromotive force is greatly changed depending on the change in concentration of oxygen contained in the combustion gas as the measurement gas, as well as in that the change in electromotive force is small with respect to the change in concentration of NOx, and hence the sensor tends to be affected by noise.

On the other hand, in order to induce the NOx-reducing ability, it is indispensable to use a reducing gas such as CO. In general, under a fuel-lean combustion condition in which a large amount of NOx is produced, the amount of produced CO is smaller than the amount of produced NOx. Therefore, the conventional gas sensor has a drawback that it cannot perform measurement for a combustion gas formed under the combustion condition as described above.

Japanese Laid-Open Patent Publication Nos. 63-38154 and 64-39545 disclose a system in which a set of electrochemical pumping cell and sensor cell comprising Pt electrodes and an oxygen ion-conductive solid electrolyte and another set of electrochemical pumping cell and sensor cell comprising Rh electrodes and an oxygen ion-conductive solid electrolyte are combined to measure NOx on the basis of the difference between pumping current values of the respective ones.

Japanese Laid-Open Patent Publication Nos. 1-277751 and 2-1543 suggest a method in which two sets, i.e., two pairs of electrochemical pumping cells and sensor cells are prepared. A sensor, which comprises one set of the pumping cell and the sensor cell, is used to measure a limiting pumping current at a partial pressure of oxygen at which NOx is not reduced. A sensor, which comprises the other set of the pumping cell and the sensor cell, is used to measure a limiting pumping current at a partial pressure of oxygen at which NOx is reduced. The difference between the measured limiting currents is measured. Alternatively, a method is suggested in which the difference in limiting current is measured by using a sensor comprising a set of pumping cell and sensor cell, while switching the partial pressure of oxygen in a measurement gas between a partial pressure of oxygen at which NOx is reduced and a partial pressure of oxygen at which NOx is not reduced.

However, in the foregoing systems for measuring NOx, the greater part of the value of the limiting current is occupied by a current brought about by oxygen which is contained in a large amount, and a current based on the objective NOx is extremely small in ordinary cases. As a result, a small current value corresponding to NOx is determined from a difference between the two large current values. Therefore, in the case of the measuring system based on the switching while using one set of sensor, continuous measurement is unsuccessful in some cases. Further, for example, such a system involves problems in that the response is slow, and the accuracy is inferior.

In the case of the system in which the two sets of sensors are used, an error tends to occur in the measured value when the oxygen concentration in the measurement gas greatly changes. Such a system cannot be used in some cases, for example, for automobiles in which the oxygen concentration in the measurement gas greatly changes. This inconvenience results from the fact that the dependency on oxygen concentration of the pumping current of one sensor is mutually different from the dependency on oxygen concentration of the pumping current of the other sensor.

For example, in the case of an automobile, the oxygen concentration in exhaust gas is several % under a driving condition of an air-fuel ratio of 20, while the NOx concentration is several hundreds ppm. Therefore, NOx has a concentration of about 1/100 of that of oxygen. In this case, only if the dependency on oxygen concentration of the pumping current slightly differs, the difference in limiting current value with respect to the change in oxygen concentration becomes larger than an amount of change in limiting current caused by NOx to be measured.

In addition, the foregoing sensor has had the following inconveniences. Namely, when a diffusion rate-determining means for the pumping cell is clogged with burned products of oil contained in exhaust gas, then a change occurs in the pumping current, and the accuracy is deteriorated. Further, when the temperature of exhaust gas is greatly changed, an abnormal factor arises in the measured value.

Moreover, the system comprising the two sets of sensors has had the following drawback. Namely, if a difference occurs between chronological changes in respective characteristics of the sensors, the difference exactly provides an error, and the system cannot be used for a long period of time.

As described above, oxygen existing in the measurement gas involves various problems on the NOx measurement. Further, oxygen arises similar problems such as decrease in measurement accuracy when measurement gas components other than NOx are measured. It has been strongly demanded to solve these problems.

The present inventors have disclosed, in Japanese Laid-Open Patent Publication No. 8-271476, a new measuring system based on the use of first and second electrochemical pumping cells arranged in series, in which a measurement gas component having bound oxygen such as NOx in a measurement gas can be measured accurately in a continuous manner with good response for a long period of time without being affected by the oxygen concentration or the change thereof in the measurement gas.

The measuring system, which has been illustratively proposed, will be briefly explained especially for its measuring procedure. At first, a measurement gas, which contains a gas component having bound oxygen to be measured, is successively introduced into first and second processing zones under predetermined diffusion resistances respectively from an external measurement gas-existing space.

In the first processing zone, oxygen in the atmosphere is pumped out by using the fist electrochemical pumping cell. Thus the value of partial pressure of oxygen is controlled to be low, at which the measurement for the amount of the objective component is not substantially affected.

In the second processing zone, the measurement gas component in the atmosphere, which has been introduced from the first processing zone, is reduced or decomposed. Oxygen produced during this process is pumped out by the aid of the oxygen-pumping action effected by the second electrochemical pumping cell.

A pumping current, which flows through the second electrochemical pumping cell, is detected to obtain a detected value from which the amount of the objective component in the measurement gas is determined.

However, as a result of further investigations on the illustratively proposed measuring system, the following problem has been revealed. Namely, when the oxygen concentration in the measurement gas is increased, the partial pressure of oxygen in the atmosphere introduced from the first processing zone to the second processing zone is changed (increased), although the oxygen concentration (partial pressure) in the atmosphere in the first processing zone is controlled by adjusting the pumping voltage of the first electrochemical pumping cell so that the electromotive force detected for the first processing zone by an oxygen partial pressure-detecting means (electrochemical sensor cell) has a constant value.

Namely, when the oxygen concentration in exhaust gas increases, the decomposing current for NO in the second processing zone also increases. As a result, it is feared that the improvement in measurement accuracy undergoes a limit.

The foregoing phenomenon is caused as follows. Namely, even when the oxygen concentration in the first processing zone is controlled to be constant by using the first electrochemical pumping cell in the first processing zone, if the oxygen concentration in exhaust gas greatly changes, for example, by a degree of 0 to 20%, then the distribution of oxygen concentration in the first processing zone changes, and the concentration of oxygen which enters the second processing zone changes.

Accordingly, if the pumping ability of the first electrochemical pumping cell is increased in the first processing zone, the change in concentration of oxygen which enters the second processing zone can be decreased. However, such a countermeasure involves various problems.

Specifically, in order to enhance the pumping ability, those conceivable include, for example, a method to enlarge the area of the pumping electrode, and a method to raise the temperature of the pump. However, if the area of the pumping electrode is enlarged, the area (volume) of the first processing zone is necessarily increased. As a result, it is feared that the response is delayed. On the other hand, if the operating temperature of the pump is raised, reduction of the measurement gas component, for example, NOx tends to occur, or decomposition of NO tends to occur on the pumping electrode in the first processing zone. As a result, it is feared that the sensitivity to NO is lowered.

SUMMARY OF THE INVENTION

The present invention has been made taking such problems into consideration, an object of which is to provide a gas sensor which makes it possible to avoid interference exerted on the NO sensitivity by the change in oxygen concentration in exhaust gas and improve the measurement accuracy for a measurement gas component, starting from the gas sensor having excellent performance illustratively proposed as described above.

In order to achieve the object as described above, the present invention lies in a gas sensor for determining an amount of a specified component in a measurement gas by reducing or decomposing the component having bound oxygen in the measurement gas and measuring an amount of oxygen produced during the reduction or decomposition, the gas sensor comprising substrates composed of solid electrolytes, a first diffusion rate-determining section for introducing the measurement gas under a predetermined diffusion resistance, a first internal space for making communication with an atmosphere of the measurement gas via the first diffusion rate-determining section, a first electrochemical pumping cell comprising the solid electrolyte for constructing the first internal space and a pair of first pumping electrodes provided in contact therewith, a first electrochemical sensor cell comprising the solid electrolyte for constructing the first internal space and a pair of first measuring electrodes provided in contact therewith, a second diffusion rate-determining section for introducing, under a predetermined diffusion resistance, the gas adjusted to have a predetermined value of oxygen concentration in the first internal space, a second internal space for making communication with the atmosphere of the measurement gas via the second diffusion rate-determining section, a second electrochemical pumping cell comprising the solid electrolyte for constructing the second internal space and a pair of second pumping electrodes provided in contact therewith, a second electrochemical sensor cell comprising the solid electrolyte for constructing the second internal space and a pair of second measuring electrodes provided in contact therewith, a third diffusion rate-determining section for introducing, under a predetermined diffusion resistance, the gas adjusted to have a predetermined value of oxygen concentration in the second internal space, a third electrochemical pumping cell for pumping out oxygen produced by reduction or decomposition of the component having bound oxygen in the measurement gas introduced via the third diffusion rate-determining section, and a current-detecting means for detecting a pumping current which is allowed to flow in accordance with operation of the third electrochemical pumping cell.

According to the present invention, the measurement gas is firstly introduced into the first internal space under the predetermined diffusion resistance via the first diffusion rate-determining section. The measurement gas introduced into the first internal space is adjusted to have the predetermined oxygen concentration by the aid of the pumping action effected by the first electrochemical pumping cell.

The gas, which has been adjusted to have the predetermined oxygen concentration by the aid of the first electrochemical pumping cell, is introduced into the second internal space under the predetermined diffusion resistance via the second diffusion rate-determining section. The gas introduced into the second internal space is finely adjusted to have the predetermined oxygen concentration by the aid of the pumping action effected by the second electrochemical pumping cell.

The gas, which has been finely adjusted to have the predetermined oxygen concentration by the aid of the second electrochemical pumping cell, is introduced into the third electrochemical pumping cell under the predetermined diffusion resistance via the third diffusion rate-determining section. The third electrochemical pumping cell performs the operation so that the component having bound oxygen in the introduced measurement gas is reduced or decomposed, and oxygen produced by the reduction or decomposition is pumped out.

The pumping current, which is allowed to flow in accordance with the operation (pumping out of the oxygen) effected by the third electrochemical pumping cell, is detected by the current-detecting means. The amount of the specified component in the measurement gas is determined on the basis of the detected value.

When the oxygen concentration in the measurement gas is greatly changed (in a range of 0 to 20%) during the period in which the foregoing operation is performed, then the distribution of oxygen concentration in the measurement gas introduced into the first internal space is greatly changed, and the amount of oxygen introduced into the second internal space is also changed.

The concentration of oxygen introduced into the second internal space is finely adjusted by the second electrochemical pumping cell. However, owing to the pumping operation effected by the first electrochemical pumping cell in the first internal space, the change in concentration of oxygen introduced into the second internal space is greatly reduced as compared with the change in concentration of oxygen in the measurement gas (the measurement gas introduced into the first internal space). Therefore, it is possible to accurately control the oxygen concentration in the second internal space to be constant.

In the present invention, the pumping operation effected by the second electrochemical pumping cell is subjected to feedback control based on the use of the second electrochemical sensor cell provided for the second internal space. Thus it is possible to more accurately control the oxygen concentration in the second internal space.

As described above, the oxygen concentration is accurately controlled to be constant in the second internal space. Accordingly, the concentration of oxygen introduced into the third electrochemical pumping cell scarcely suffers the influence exerted by the change in oxygen concentration in the measurement gas (the measurement gas introduced into the first internal space). As a result, the pumping current value, which is detected by the current-detecting means in accordance with the pumping out for the oxygen effected by the third electrochemical pumping cell, is not affected by the change in concentration of oxygen in the measurement gas. The pumping current value is a value which accurately corresponds to the amount of the objective component existing in the measurement gas.

Namely, the gas sensor according to the present invention makes it possible to avoid interference exerted by the change in concentration of oxygen in exhaust gas on the detecting sensitivity for the amount of the objective component existing in the measurement gas. Thus it is possible to improve the measurement accuracy for the measurement gas component.

In a preferred embodiment, the gas sensor according to the present invention further comprises a third internal space which communicates with the atmosphere of the measurement gas via the third diffusion rate-determining section, wherein the third electrochemical pumping cell comprises the solid electrolyte for constructing the third internal space and a pair of third pumping electrodes provided in contact therewith.

In this embodiment, the oxygen concentration is accurately controlled to be constant in the second internal space. Accordingly, the concentration of oxygen introduced into the third internal space is scarcely affected by the change in oxygen concentration in the measurement gas (the measurement gas introduced into the first internal space). As a result, the pumping current value, which is detected by the current-detecting means in accordance with the pumping out for the oxygen effected by the third electrochemical pumping cell provided for the third internal space, is not affected by the change in concentration of oxygen in the measurement gas. The pumping current value is a value which accurately corresponds to the amount of the objective component existing in the measurement gas.

In another preferred embodiment of the gas sensor according to the present invention, the third electrochemical pumping cell comprises the solid electrolyte for constructing the second internal space and a pair of third pumping electrodes provided in contact therewith.

In this embodiment, it is unnecessary to provide a new internal space for providing the third electrochemical pumping cell. Therefore, it is possible to facilitate miniaturization of the entire structure of the gas sensor.

In still another embodiment of the gas sensor constructed as described above, it is preferable that the second measuring electrode and the third pumping electrode provided for the second internal space, of the pair of second measuring electrodes and the pair of third pumping electrodes, are arranged opposingly to one another.

In this embodiment, when the concentration of the measurement gas component is measured on the basis of the pumping current, the second measuring electrode and the third pumping electrode are in a relational arrangement in which the former is scarcely affected by the latter. Therefore, even when the third electrochemical pumping cell is provided in the second internal space, the amount of the objective component existing in the measurement gas can be accurately measured.

In the gas sensor constructed as described above, it is preferable that the second pumping electrode and the second measuring electrode provided for the second internal space, of the pair of second pumping electrodes and the pair of second measuring electrodes, are combined into a common electrode.

In this embodiment, it is unnecessary to give a broad area in order to form the electrode in the second internal space. Accordingly, it is possible to miniaturize the structure of the gas sensor itself. When the gas sensor is designed to have an identical size, it is possible to give a wide volume of the first internal space. Thus it is possible to enhance the pumping function of the second electrochemical pumping cell, and it is possible to more accurately perform fine adjustment for the oxygen concentration in the second internal space.

Owing to the common structure of the pumping electrode and the measuring electrode, for example, when the amount of pumping out of oxygen effected by the second electrochemical pumping cell in the second internal space changes, and the oxygen concentration in the second internal space changes, then the measured voltage in the second electrochemical sensor cell also changes without any time delay. Accordingly, the second electrochemical pumping cell can be subjected to feedback control effected by the second electrochemical sensor cell in an appropriate manner without involving any oscillation.

In the gas sensor described above, it is preferable that a material having lowered reducing ability or having no reducing ability for NO in the measurement gas is used as a material for the first pumping electrode and the first measuring electrode disposed in the first internal space and for the second pumping electrode and the second measuring electrode disposed in the second internal space. In this embodiment, those usable as the material having lowered reducing ability or having no reducing ability for NO in the measurement gas include a cermet of Au and $ZrO_2$ and a cermet of Au, an alloy of Pt group element, and $ZrO_2$.

In another aspect, the present invention lies in a gas sensor for determining an amount of a specified component in a measurement gas by reducing or decomposing the component having bound oxygen in the measurement gas and measuring an amount of oxygen produced during the reduction or decomposition, the gas sensor comprising substrates composed of solid electrolytes, a first diffusion rate-determining section for introducing the measurement gas under a predetermined diffusion resistance, a first internal space for making communication with an atmosphere of the measurement gas via the first diffusion rate-determining section, a first electrochemical pumping cell comprising the solid electrolyte for constructing the first internal space and a pair of first pumping electrodes provided in contact therewith, a first electrochemical sensor cell comprising the solid electrolyte for constructing the first internal space and a pair of first measuring electrodes provided in contact therewith, a second diffusion rate-determining section for introducing, under a predetermined diffusion resistance, the gas adjusted to have a predetermined value of oxygen concentration in the first internal space, a second internal space for making communication with the atmosphere of the measurement gas via the second diffusion rate-determining section, a second electrochemical pumping cell comprising the solid electrolyte for constructing the second internal space and a pair of second pumping electrodes provided in contact therewith, a second electrochemical sensor cell comprising the solid electrolyte for constructing the second internal space and a pair of second measuring electrodes provided in contact therewith, a third diffusion rate-determining section for introducing, under a predetermined diffusion resistance, the gas adjusted to have a predetermined value of oxygen concentration in the second internal space, a third electrochemical sensor cell for outputting an electromotive force corresponding to a partial pressure of oxygen defined by oxygen produced by reduction or decomposition of the component having bound oxygen in the measurement gas introduced via the third diffusion rate-determining section, and a voltage-detecting means for detecting the electromotive force outputted from the third electrochemical sensor cell.

According to the present invention, the measurement gas is firstly introduced into the first internal space under the predetermined diffusion resistance via the first diffusion rate-determining section. The measurement gas introduced into the first internal space is adjusted to have the predetermined oxygen concentration by the aid of the pumping action effected by the first electrochemical pumping cell.

The gas, which has been adjusted to have the predetermined oxygen concentration by the aid of the first electrochemical pumping cell, is introduced into the second internal space under the predetermined diffusion resistance via the second diffusion rate-determining section. The gas introduced into the second internal space is finely adjusted to have the predetermined oxygen concentration by the aid of the pumping action effected by the second electrochemical pumping cell.

The gas, which has been finely adjusted to have the predetermined oxygen concentration by the aid of the second electrochemical pumping cell, is introduced into the third electrochemical sensor cell under the predetermined diffusion resistance via the third diffusion rate-determining section. The third electrochemical sensor cell reduces or decomposes the component having bound oxygen in the introduced measurement gas, and it outputs the electromotive force corresponding to the partial pressure of oxygen defined by oxygen produced during the reduction or decomposition.

The electromotive force outputted from the third electrochemical sensor cell is detected by the voltage-detecting means. The amount of the specified component in the measurement gas is determined on the basis of the detected value (voltage value).

When the oxygen concentration in the measurement gas is greatly changed (in a range of 0 to 20%) during the period in which the foregoing operation is performed, then the distribution of oxygen concentration in the measurement gas introduced into the first internal space is greatly changed, and the amount of oxygen introduced into the second internal space is also changed.

The concentration of oxygen introduced into the second internal space is finely adjusted by the second electrochemical pumping cell. However, owing to the pumping operation effected by the first electrochemical pumping cell in the first internal space, the change in concentration of oxygen introduced into the second internal space is greatly reduced as compared with the change in concentration of oxygen in the measurement gas (the measurement gas introduced into the first internal space). Therefore, it is possible to accurately control the oxygen concentration in the second internal space to be constant.

In the present invention, the pumping operation effected by the second electrochemical pumping cell is subjected to feedback control on the basis of the second electrochemical sensor cell provided for the second internal space. Thus it is possible to more accurately control the oxygen concentration in the second internal space.

As described above, the oxygen concentration is accurately controlled to be constant in the second internal space. Accordingly, the concentration of oxygen introduced into the third electrochemical pumping cell scarcely suffers the influence exerted by the change in oxygen concentration in the measurement gas (the measurement gas introduced into the first internal space). As a result, the voltage value, which is detected by the voltage-detecting means, is not affected by the change in concentration of oxygen in the measurement gas. The voltage value is a value which accurately corresponds to the amount of the objective component existing in the measurement gas.

Namely, the gas sensor according to this aspect of the present invention makes it also possible to avoid interference exerted by the change in concentration of oxygen in exhaust gas on the detecting sensitivity for the amount of the objective component existing in the measurement gas. Thus it is possible to improve the measurement accuracy for the measurement gas component.

Especially, in the gas sensor according to the present invention, the third electrochemical sensor cell outputs the electromotive force corresponding to the partial pressure of oxygen defined by oxygen produced by the reduction or decomposition of the measurement gas component. The electromotive force is detected as the voltage value by the voltage-detecting means provided for the downstream stage. Therefore, even when oxygen is produced in a slight amount upon measurement for a measurement gas component at a low concentration, the slight amount of oxygen can be measured as a large change in electromotive force. Accordingly, it is possible to realize high S/N for the detecting sensitivity.

In a preferred embodiment, the gas sensor according to the present invention further comprises a third internal space which communicates with the atmosphere of the measurement gas via the third diffusion rate-determining section, wherein the third electrochemical sensor cell comprises the solid electrolyte for constructing the third internal space and a pair of third measuring electrodes provided in contact therewith.

In this embodiment, the third electrochemical sensor cell outputs the electromotive force corresponding to the partial pressure of oxygen in the atmosphere in the third internal space defined by oxygen produced by the reduction of decomposition of the measurement gas component. In conjunction with the fact that the oxygen concentration is accurately controlled to be constant in the second internal space, the concentration of oxygen introduced into the third internal space is scarcely affected by the change in oxygen concentration in the measurement gas (the measurement gas introduced into the first internal space). As a result, the voltage value, which is detected by the voltage-detecting means, is not affected by the change in concentration of oxygen in the measurement gas. The voltage value is a value which accurately corresponds to the amount of the objective component existing in the measurement gas.

In another preferred embodiment of the gas sensor according to the present invention, the third electrochemical sensor cell comprises the solid electrolyte for constructing the second internal space and a pair of third measuring electrodes provided in contact therewith.

In this embodiment, it is unnecessary to provide a new internal space for providing the third electrochemical sensor cell. Therefore, it is possible to facilitate miniaturization of the entire structure of the gas sensor.

In the gas sensor constructed as described above, it is preferable that the third measuring electrode provided for the second internal space, of the pair of third measuring electrodes is exposed to the inside of the second internal space. Namely, the third diffusion rate-determining section may be omitted. In other words, the third diffusion rate-determining section can be omitted by appropriately adjusting the relational arrangement of the second pumping electrode and the third measuring electrode in the second internal space. In this embodiment, it is unnecessary to form the third diffusion rate-determining section so that it surrounds the third measuring electrode. Therefore, it is possible to simplify the production steps.

In still another embodiment of the gas sensor constructed as described above, it is preferable that the second measuring electrode and the third measuring electrode provided for the second internal space, of the pair of second measuring electrodes and the pair of third measuring electrodes, are arranged in parallel to one another.

In this embodiment, when the concentration of the measurement gas component is measured on the basis of the electromotive force, the second measuring electrode and the third measuring electrode are disposed adjacent to one another. Therefore, it is possible to more accurately control the oxygen concentration in the vicinity of the second measuring electrode. Even when the third electrochemical sensor cell is provided in the second internal space, the amount of the objective component existing in the measurement gas can be accurately measured.

In the gas sensor constructed as described above, it is preferable that the second pumping electrode and the second measuring electrode provided for the second internal space, of the pair of second pumping electrodes and the pair of second measuring electrodes, are combined into a common electrode.

In this embodiment, it is unnecessary to give a broad area in order to form the electrode in the second internal space. Accordingly, it is possible to miniaturize the structure of the gas sensor itself. When the gas sensor is designed to have an identical size, it is possible to give a wide volume of the second internal space. Thus it is possible to enhance the pumping function of the second electrochemical pumping cell, and it is possible to more accurately perform fine adjustment for the oxygen concentration in the second internal space.

Owing to the common structure of the pumping electrode and the measuring electrode, for example, when the amount of pumping out of oxygen effected by the second electrochemical pumping cell in the second internal space changes, and the oxygen concentration in the second internal space changes, then the measured voltage in the second electrochemical sensor cell also changes without any time delay. Accordingly, the second electrochemical pumping cell can be subjected to feedback control effected by the second electrochemical sensor cell in an appropriate manner without involving any oscillation.

In the gas sensor described above, it is preferable that a material having lowered reducing ability or having no reducing ability for NO in the measurement gas is used as a material for the first pumping electrode and the first measuring electrode disposed in the first internal space and for the second pumping electrode and the second measuring electrode disposed in the second internal space. In this embodiment, those usable as the material having lowered reducing ability or having no reducing ability for NO in the measurement gas include a cermet of Au and $ZrO_2$ and a cermet of Au, an alloy of Pt group element, and $ZrO_2$.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 11 shows a cross-sectional view taken along a line XI—XI in FIG. 10.

DESCRIPTION OF THE PREFERRED EMBODIMENTS

Several illustrative embodiments, in which the gas sensor according to the present invention is applied to gas sensors for measuring oxides such as NO, $NO_2$, $SO_2$, $CO_2$, and $H_2O$ and inflammable gases such as CO and CnHm contained, for example, in atmospheric air and exhaust gas discharged from vehicles or automobiles, will be explained with reference to FIGS. 1 to 11.

Figure 1:
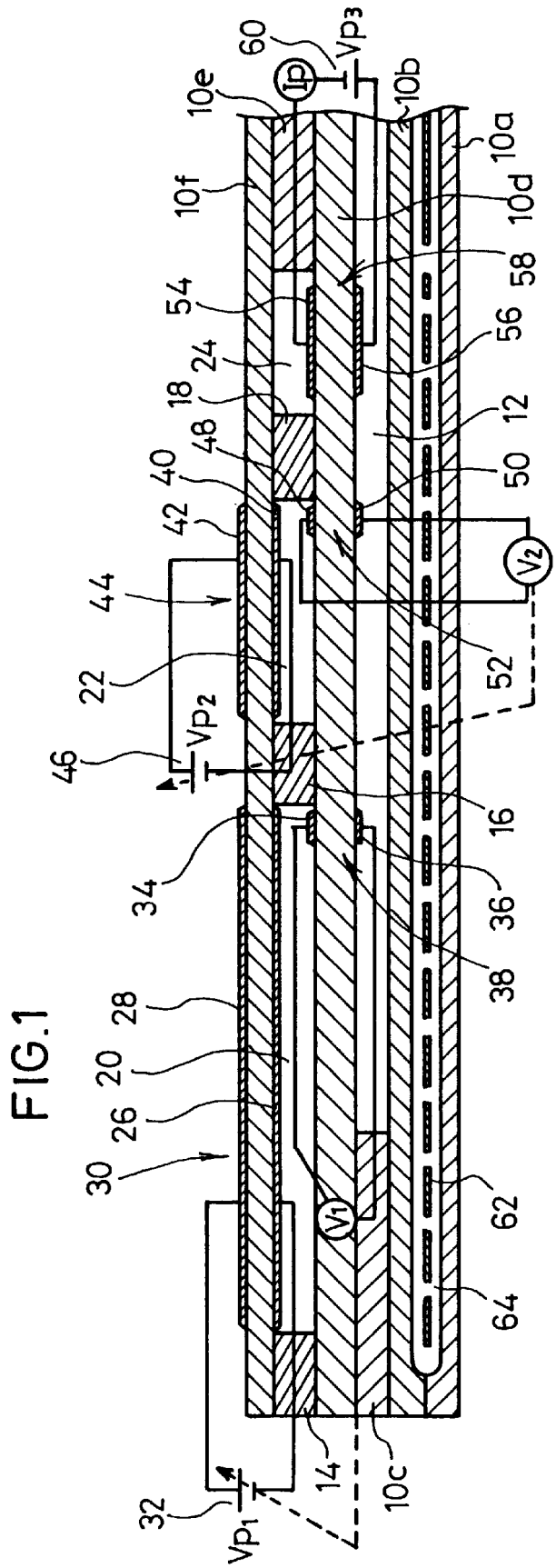
FIG. 1 shows a schematic cross-sectional view illustrating an arrangement of a gas sensor according to a first embodiment.

As shown in FIG. 1, a gas sensor according to a first embodiment comprises, for example, six stacked solid electrolyte layers 10a to 10f each composed of a ceramic based on the use of an oxygen ion-conductive solid electrolyte such as $ZrO_2$. First and second layers from the bottom are designated as first and second substrate layers 10a, 10b, third and fifth layers from the bottom are designated as first and second spacer layers 10c, 10e, and fourth and sixth layers from the bottom are designated as first and second solid electrolyte layers 10d, 10f.

Specifically, the first spacer layer 10c is stacked on the second substrate layer 10b. The first solid electrolyte layer 10d, the second spacer layer 10e, and the second solid electrolyte layer 10f are successively stacked on the first spacer layer 10c.

A space (reference gas-introducing space 12), into which a reference gas such as atmospheric air to serve as a reference for measuring oxides is introduced, is comparted and formed between the second substrate layer 10b and the first solid electrolyte layer 10d, by a lower surface of the first solid electrolyte layer 10d, an upper surface of the second substrate layer 10b, and side surfaces of the first spacer layer 10c.

The second spacer layer 10e is interposed between the first and second solid electrolyte layers 10d, 10f, and first, second, and third diffusion rate-determining sections 14, 16, 18 are interposed therebetween.

A first internal space 20 for adjusting the partial pressure of oxygen in the measurement gas is comparted and formed by a lower surface of the second solid electrolyte layer 10f, side surfaces of the first and second diffusion rate-determining sections 14, 16, and an upper surface of the first solid electrolyte layer 10d. A second internal space 22 for finely adjusting the partial pressure of oxygen in the measurement gas is comparted and formed by the lower surface of the second solid electrolyte layer 10f, side surfaces of the second and third diffusion rate-determining sections 16, 18, and the upper surface of the first solid electrolyte layer 10d. A third internal space 24 for measuring oxides, for example, nitrogen oxides (NOx) in the measurement gas is comparted and formed by the lower surface of the second solid electrolyte layer 10f, a side surface of the third diffusion rate-determining section 18, side surfaces of the second spacer layer 10e, and the upper surface of the first solid electrolyte layer 10d.

The external space is allowed to communicate with the first internal space 20 via the first diffusion rate-determining section 14. The first internal space is allowed to communicate with the second internal space 22 via the second diffusion rate-determining section 16. The second internal space 22 is allowed to communicate with the third internal space 24 via the third diffusion rate-determining section 18.

The first, second, and third diffusion rate-determining sections 14, 16, 18 give predetermined diffusion resistances to the measurement gas introduced into the first internal space 20, the second internal space 22, and the third internal space 24 respectively. Each of the diffusion rate-determining sections 14, 16, 18 can be formed as a passage composed of, for example, a porous material, or a small hole having a predetermined cross-sectional area through which the measurement gas can be introduced.

Especially, a porous member composed of, for example, $ZrO_2$ is charged and arranged in the second and third diffusion rate-determining sections 16, 18. Thus the diffusion resistances of the second and third diffusion rate-determining sections 16, 18 are made larger than the diffusion resistance of the first diffusion rate-determining section 14.

The atmosphere in the first internal space 20 is introduced into the second internal space 22 under the predetermined diffusion resistance via the second diffusion rate-determining section 16. Further, the atmosphere in the second internal space 22 is introduced into the third internal space 24 under the predetermined diffusion resistance.

A first inner pumping electrode 26 having an approximately rectangular planar configuration and composed of a porous cermet electrode is formed on an entire surface portion of the lower surface of the second solid electrolyte layer 1f for forming the first internal space 20. A first outer pumping electrode 28 is formed on a portion of the upper surface of the second solid electrolyte layer 10f, the portion corresponding to the first inner pumping electrode 26. A first electrochemical pumping cell 30 is constructed by the first inner pumping electrode 26, the first outer pumping electrode 28, and the second solid electrolyte layer 10f.

A desired voltage Vp1 is applied by the aid of an external variable power source 32 between the first inner pumping electrode 26 and the first outer pumping electrode 28 of the first electrochemical pumping cell 30 so that a pumping current is allowed to flow in a direction from the first outer pumping electrode 28 to the first inner pumping electrode 26. Thus oxygen in the atmosphere in the first internal space 20 can be pumped out to the external space at the outside.

A first measuring electrode 34 having an approximately rectangular planar configuration and composed of a porous cermet electrode is formed on a portion of the upper surface of the first solid electrolyte layer 10d for forming the first internal space 20, the portion being adjacent to the second diffusion rate-determining section 16. A first reference electrode 36 is formed on a portion of the lower surface of the first solid electrolyte layer 10d, the portion being exposed to the reference gas-introducing space 12 and corresponding to the first measuring electrode 34. A first electrochemical sensor cell 38, which serves as an oxygen partial pressure-detecting means, is constructed by the first measuring electrode 34, the first reference electrode 36, and the first solid electrolyte layer 10d.

The first electrochemical sensor cell 38 is operated to measure, with a voltmeter V1, an electromotive force generated between the first measuring electrode 34 and the first reference electrode 36 on the basis of a difference in oxygen concentration between the atmosphere in the first internal space 20 and the reference gas (atmospheric air) in the reference gas-introducing space 12. Thus the partial pressure of oxygen in the atmosphere in the first internal space 20 can be detected.

A detected value of the partial pressure of oxygen is used to perform feedback control for the variable power source 32. Specifically, the pumping action of the first electrochemical pumping cell 30 is controlled so that the partial pressure of oxygen in the atmosphere in the first internal space 20 has a predetermined value which is sufficiently low to perform control of the partial pressure of oxygen in the next internal space 22.

The porous cermet electrode for constructing the first inner pumping electrode 26 and the first outer pumping electrode 28 is composed of a metal such as Pt and a ceramic such as $ZrO_2$. However, it is necessary that a material having weakened reducing ability or having no reducing ability for the NO component in the measurement gas is used for the first inner pumping electrode 26 and the first measuring electrode 34 which are arranged in the first internal space 20 and which make contact with the measurement gas. It is preferable that the first inner pumping electrode 26 and the first measuring electrode 34 are composed of, for example, a compound having the perovskite structure such as $La_3CuO_4$, a cermet of a ceramic and a metal having low catalytic activity such as Au, or a cermet of a ceramic, a Pt group metal, and a metal having low catalytic activity such as Au. When an alloy of Au and a Pt group metal is used as an electrode material, it is preferable to add Au in an amount of 0.03 to 35 vol % of the entire metal component.

A second inner pumping electrode 40 having an approximately rectangular planar configuration and composed of a porous cermet electrode is formed on an entire surface portion of the lower surface of the second solid electrolyte layer 10f for forming the second internal space 22. A second outer pumping electrode 42 is formed on a portion of the upper surface of the second solid electrolyte layer 10f, the portion corresponding to the second inner pumping electrode 40. A second electrochemical pumping cell 44 is constructed by the second inner pumping electrode 40, the second outer pumping electrode 42, and the second solid electrolyte layer 10f.

A desired voltage Vp2 is applied by the aid of an external variable power source 46 between the second inner pumping electrode 40 and the second outer pumping electrode 42 of the second electrochemical pumping cell 44 so that a current is allowed to flow in a direction from the second outer pumping electrode 42 to the second inner pumping electrode 40. Thus oxygen in the atmosphere in the second internal space 22 can be pumped out to the external space. Accordingly, the partial pressure of oxygen in the atmosphere in the second internal space 22 is controlled to have a low value of the partial pressure of oxygen at which measurement for the amount of the objective component is not substantially affected, under the condition in which the measurement gas component (NOx) is not substantially reduced or decomposed. In this arrangement, owing to the operation of the first electrochemical pumping cell 30 disposed for the first internal space 20, the change in amount of oxygen introduced into the second internal space 22 is greatly reduced as compared with the change in the measurement gas. Therefore, the partial pressure of oxygen in the second internal space 22 is accurately controlled to be constant.

In the gas sensor according to the first embodiment, a second measuring electrode 48 having an approximately rectangular planar configuration and composed of a porous cermet electrode is formed on a portion of the upper surface of the first solid electrolyte layer 10d for forming the second internal space 22, the portion being adjacent to the third diffusion rate-determining section 18. A second reference electrode 50 is formed on a portion of the lower surface of the first solid electrolyte layer 10d, the portion being exposed to the reference gas-introducing space 12 and corresponding to the second measuring electrode 48. A second electrochemical sensor cell 52, which serves as an oxygen partial pressure-detecting means, is constructed by the second measuring electrode 48, the second reference electrode 50, and the first solid electrolyte layer 10d.

The second electrochemical sensor cell 52 is operated to measure, with a voltmeter V2, an electromotive force generated between the second measuring electrode 48 and the second reference electrode 50 on the basis of a difference in oxygen concentration between the atmosphere in the second internal space 22 and the reference gas (atmospheric air) in the reference gas-introducing space 12. Thus the partial pressure of oxygen in the atmosphere in the second internal space 22 can be detected.

A detected value of the partial pressure of oxygen is used to perform feedback control for the variable power source 46. Thus the partial pressure of oxygen in the second internal space 22 is more accurately controlled by the second electrochemical pumping cell 44.

Further, in the gas sensor according to the first embodiment, a third inner pumping electrode 54 having an approximately rectangular planar configuration and composed of a porous cermet electrode is formed on an approximately entire surface portion of the upper surface of the first solid electrolyte layer 10d for forming the third internal space 24. A third outer pumping electrode 56 is formed on a portion of the lower surface of the first solid electrolyte layer 10d, the portion being exposed to the reference gas-introducing space 12 and corresponding to the third inner pumping electrode 54. A third electrochemical pumping cell 58 is constructed by the third inner pumping electrode 54, the third outer pumping electrode 56, and the first solid electrolyte layer 10d.

The third inner pumping electrode 54 is composed of a porous cermet comprising zirconia as a ceramic and Rh as a metal capable of reducing NOx which is the measurement gas component. Accordingly, the third inner pumping electrode 54 functions as a NOx-reducing catalyst for reducing NOx existing in the atmosphere in the third internal space 24. Further, the third inner pumping electrode 54 serves to pump out oxygen in the atmosphere in the third internal space 24 to the reference gas-introducing space 12 in accordance with a constant voltage Vp3 applied between the third inner pumping electrode 54 and the third outer pumping electrode 56, by the aid of a DC power source 60. The pumping current, which is allowed to flow in accordance with the pumping action of the third electrochemical pumping cell 58, is detected by an ammeter Ip.

The constant voltage (DC) power source 60 can apply a voltage having a magnitude to give a limiting current to the pumping for oxygen produced during the decomposition effected by the third electrochemical pumping cell 58, under the inflow of NOx restricted by the third diffusion rate-determining section 18.

The gas sensor according to the first embodiment further comprises a heater 62 for generating heat by the aid of external power supply. The heater 62 is embedded in a form of being vertically interposed between the first and second substrate layers 10a, 10b. The heater 62 is provided to enhance the oxygen ion conductivity. A ceramic layer 64 composed of alumina or the like is formed on upper and lower surfaces of the heater 62, for electrically insulating the heater 62 from the substrate layers 10a, 10b.

As shown in FIG. 1, the heater 62 is arranged over the entire area ranging from the first internal space 20 to the third internal space 24. Thus the respective internal spaces 20, 22, 24 are heated to predetermined temperatures respectively. Further, the first, second, and third electrochemical pumping cells 30, 44, 58, and the first and second electrochemical sensor cells 38, 52 are also heated to and maintained at predetermined temperatures respectively.

The gas sensor according to the first embodiment is placed so that its forward end is disposed on the side of the external space. Accordingly, the measurement gas is introduced into the first internal space 20 under the predetermined diffusion resistance via the first diffusion rate-determining section 14. The measurement gas introduced into the first internal space 20 undergoes the oxygen-pumping action caused by applying the predetermined voltage Vp1 between the pair of pumping electrodes 26, 28 for constructing the first electrochemical pumping cell 30. The partial pressure of oxygen is controlled to have a predetermined value, for example, $10^{-7}$ atm.

The partial pressure of oxygen in the atmosphere in the first internal space 20 is controlled as follows so that it has the predetermined value, on the basis of the Nernst's equation. Namely, the electromotive force between the first measuring electrode 34 and the first reference electrode 36 of the first electrochemical sensor cell 38 is measured by using the voltmeter V1 to obtain a voltage value. The voltage (the variable power source 32), which is applied between the pair of pumping electrodes 26, 28 of the first electrochemical pumping cell 30, is subjected to feedback control so that the voltage value is, for example, 300 mV (700° C.). Thus the control is performed so that the objective partial pressure of oxygen of $10^{-7}$ atm is achieved.

Namely, the voltage Vp1 applied to the first electrochemical pumping cell 30 is controlled so that the electromotive force outputted from the first electrochemical sensor cell 38 is an electromotive force which corresponds to a difference between the desired oxygen concentration in the first internal space 20 and the oxygen concentration in the reference gas.

The first diffusion rate-determining section 14 serves to restrict the amount of diffusion and inflow of oxygen in the measurement gas into the measuring space (the first internal space 20) when the voltage Vp1 is applied to the first electrochemical pumping cell 30 so that the current flowing through the first electrochemical pumping cell 30 is suppressed.

A state of partial pressure of oxygen in which NOx in the atmosphere is not reduced by the first inner pumping electrode 26 and the first measuring electrode 34, i.e., for example, a condition of partial pressure of oxygen in which the reaction of NO→½N$_2$+½O$_2$ is not caused even in an environment of being heated by the external measurement gas and being heated by the heater 62 is established in the first internal space 20. This is because of the following reason. Namely, if NOx in the measurement gas (atmosphere) is reduced in the first internal space 20, it is impossible to accurately measure NOx in the third internal space 24 disposed in the downstream stage. In this context, it is necessary to establish the condition in which NOx is not reduced in the first internal space 20 by the components (the metal components of the first inner pumping electrode 26 and the first measuring electrode 34 in this case) which are possibly relevant to reduction of NOx. Specifically, this condition is achieved by using a material having low reducing ability for NOx, for example, an alloy of Au and Pt, for the first inner pumping electrode 26 and the first measuring electrode 34.

The gas in the first internal space 20 is introduced into the second internal space 22 under the predetermined diffusion resistance via the second diffusion rate-determining section 16. The gas introduced into the second internal space 22 undergoes the oxygen-pumping action caused by applying the predetermined voltage Vp2 between the pair of pumping electrodes 40, 42 for constructing the second electrochemical pumping cell 44. The gas is controlled so that its partial pressure of oxygen always has a constant low value of the partial pressure of oxygen.

The partial pressure of oxygen in the atmosphere in the second internal space 22 is controlled as follows so that it has the predetermined low value, on the basis of the Nernst's equation. Namely, the electromotive force between the second measuring electrode 48 and the second reference electrode 50 of the second electrochemical sensor cell 52 is measured by using the voltmeter V2 to obtain a voltage value. The voltage (the variable power source 46), which is applied between the pair of pumping electrodes 40, 42 of the second electrochemical pumping cell 44, is subjected to feedback control so that the voltage value is, for example, 430 mV (700° C.). Thus the control is performed so that the constant low partial pressure of oxygen is obtained.

Namely, the voltage Vp2 applied to the second electrochemical pumping cell 44 is controlled so that the electromotive force outputted from the second electrochemical sensor cell 52 is an electromotive force which corresponds to a difference between the desired oxygen concentration in the second internal space 22 and the oxygen concentration in the reference gas.

The second diffusion rate-determining section 16 serves to restrict the amount of diffusion and inflow of oxygen in the measurement gas into the measuring space (the second internal space 22) when the voltage Vp2 is applied to the second electrochemical pumping cell 44 so that the current flowing through the second electrochemical pumping cell 44 is suppressed, in the same manner as performed by the first diffusion rate-determining section 14.

A state of partial pressure of oxygen in which NOx in the atmosphere is not reduced by the second inner pumping electrode 40 and the second measuring electrode 48 even in an environment of being heated by the external measurement gas and being heated by the heater 62 is also established in the second internal space 22, in the same manner as established in the first internal space 20. Accordingly, it is also necessary for the second inner pumping electrode 40 and the second measuring electrode 48 to use a material having weakened reducing ability or having no reducing ability for the NO component in the measurement gas, in the same manner as the first inner pumping electrode 26 and the first measuring electrode 34. Preferably, for example, the electrodes are composed of a compound having the perovskite structure such as La$_3$CuO$_4$, a cermet of a ceramic and a metal having low catalytic activity such as Au, or a cermet of a ceramic, a Pt group metal, and a metal having low catalytic activity such as Au. When an alloy of Au and a Pt group metal is used as an electrode material, it is preferable to add Au in an amount of 0.03 to 35 vol % of the entire metal component.

The measurement gas, which has been controlled for the partial pressure of oxygen in the second internal space 22 as described above, is introduced into the third internal space 24 under the predetermined diffusion resistance via the third diffusion rate-determining section 18.

When it is intended to control the partial pressure of oxygen in the atmosphere in the first internal space 20 to have a low value of the partial pressure of oxygen at which the measurement for NOx is not substantially affected, by operating the first electrochemical pumping cell 30, in other words, when the voltage Vp1 of the variable power source 32 is adjusted so that the voltage detected by the first electrochemical sensor cell 38 is constant, if the oxygen concentration in the measurement gas greatly changes, for example, in a range of 0 to 20%, then the respective partial pressures of oxygen in the atmosphere in the second internal space 22 and in the atmosphere in the third internal space 24 are slightly changed in ordinary cases, probably because of the following reason. Namely, when the oxygen concentration in the measurement gas is increased, the distribution of oxygen concentration appears over the first measuring electrode 34 in the widthwise direction and in the thickness direction of the first internal space 20. The distribution of oxygen concentration changes depending on the oxygen concentration in the measurement gas.

However, in the gas sensor according to the first embodiment, the second electrochemical pumping cell 44 is provided for the second internal space 22 so that the partial pressure of oxygen in its internal atmosphere always has the constant low value of the partial pressure of oxygen. Therefore, even when the partial pressure of oxygen in the atmosphere introduced from the first internal space 20 into the second internal space 22 is changed depending on the oxygen concentration in the measurement gas, the partial pressure of oxygen in the atmosphere in the second internal space 22 is always allowed to have the constant low value owing to the pumping action effected by the second electrochemical pumping cell 44. As a result, the partial pressure of oxygen can be controlled to have a low value at which the measurement for NOx is not substantially affected.

NOx in the measurement gas introduced into the third internal space 24 is reduced or decomposed around the third inner pumping electrode 54 of the third electrochemical pumping cell 58, and for example, the reaction of NO→½N$_2$+½O$_2$ is caused. During this process, a predetermined voltage Vp3, for example, a voltage of 430 mV (700° C.) is applied between the third inner pumping electrode 54 and the third outer pumping electrode 56 for constructing the third electrochemical pumping cell 58, in a direction to pump out oxygen from the third internal space 24 to the reference gas-introducing space 12.

Therefore, the pumping current flowing through the third electrochemical pumping cell 58 has a value which is proportional to a sum of the oxygen concentration in the atmosphere introduced into the third internal space 24, i.e., the oxygen concentration in the second internal space 22 and the oxygen concentration produced by reducing or decomposing NOx by the third inner pumping electrode 54.

Figure 2:
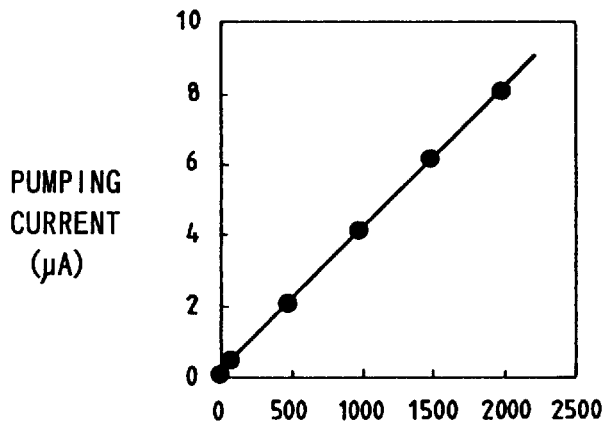
FIG. 2 shows a characteristic curve illustrating dependency on NOx concentration, of the pumping current flowing through a third electrochemical pumping cell.

In the present invention, the oxygen concentration in the atmosphere in the second internal space 22 is controlled to be constant by the aid of the second electrochemical pumping cell 44. Accordingly, as shown in FIG. 2, the pumping current flowing through the third electrochemical pumping cell 58 is proportional to the concentration of NOx. The concentration of NOx corresponds to the diffusion amount of NOx restricted by the third diffusion rate-determining section 18. Therefore, even when the oxygen concentration in the measurement gas is greatly changed, the NOx concentration can be accurately measured by means of the ammeter Ip by the aid of the third electrochemical pumping cell 58.

It is assumed, for example, that the partial pressure of oxygen in the atmosphere in the second internal space 22 controlled by the second electrochemical pumping cell 44 is 0.02 ppm, and the concentration of NO as the NOx component in the measurement gas is 100 ppm. The pumping current flows in an amount corresponding to a sum (=50.02 ppm) of the oxygen concentration of 50 ppm produced by the reduction or decomposition of NO and the oxygen concentration of 0.02 ppm in the atmosphere in the second internal space 22. Therefore, almost all parts of the pumping current value obtained in the third electrochemical pumping cell 58 represent the amount obtained by the reduction or decomposition of NO. For this reason, the pumping current value does not depend on the oxygen concentration in the measurement gas.

Figure 3:
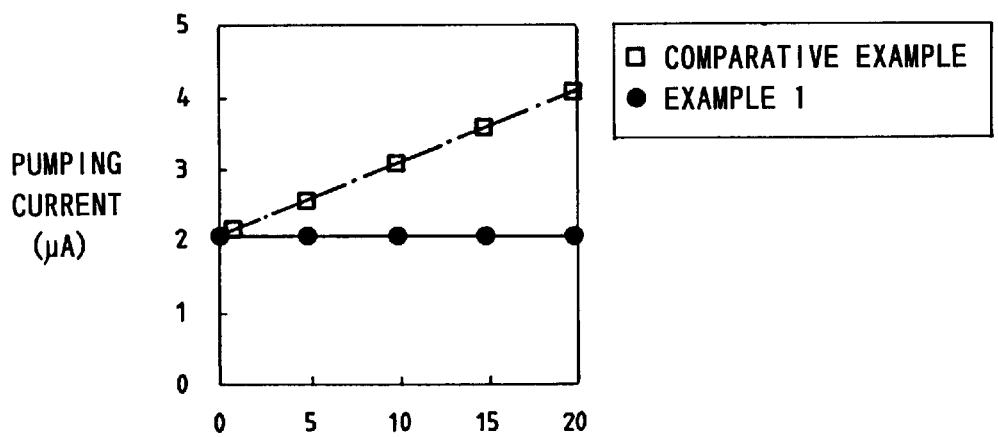
FIG. 3 shows characteristic curves illustrating the change in pumping current in the third electrochemical pumping cell, obtained when the oxygen concentration in a measurement gas was changed in a range of 0 to 20%, wherein a solid line represents the characteristic obtained in Example 1, and a chain line represents the characteristic obtained in Comparative Example.

In FIG. 3, there were prepared Example 1 concerning a gas sensor constructed in the same manner as the gas sensor according to the first embodiment, and Comparative Example concerning a gas sensor constructed without providing the second internal space 22, the second electrochemical pumping cell 44, and the second electrochemical sensor cell 52. FIG. 3 shows the change in the pumping current in the third electrochemical pumping cell 58, obtained when basic gas components were based on an N$_2$—NO—O$_2$—H$_2$O system, the concentration of NO as the NOx component was fixed to be 300 ppm, and the oxygen concentration in the measurement gas was changed in a range of 0 to 20% while using N$_2$ as a carrier gas. In FIG. 3, a characteristic curve obtained in Example 1 is represented by a solid line, and a characteristic curve obtained in Comparative Example is represented by a chain line.

In Example 1, the first electrochemical pumping cell 30 had a pumping voltage of 300 mV (700° C.), and the second and third electrochemical pumping cells 44, 58 had a pumping voltage of 430 mV (700° C.). In Comparative Example, the first electrochemical pumping cell 30 had a pumping voltage of 300 mV (700° C.), and the third electrochemical pumping cell 58 had a pumping voltage of 430 mV (700° C.).

As clarified from the result shown in FIG. 3, the change in pumping current caused by reduction or decomposition of NO was not observed in Example 1 even when the oxygen concentration in the measurement gas was changed. Therefore, it is possible to obtain an accurate pumping current value corresponding to the NO concentration, regardless of the change in oxygen concentration in the measurement gas.

On the contrary, in Comparative Example, the pumping current value in the third electrochemical pumping cell 58 was gradually increased as the oxygen concentration in the measurement gas was increased. Therefore, it is understood that it is difficult to accurately determine the NO concentration from the pumping current value.

The accurate measurement for the NO concentration successfully performed without being affected by the change in oxygen concentration in the measurement gas as described above results in the increase in S/N for the measurement sensitivity. Thus the measurement can be performed even when the measurement gas component is at a low concentration.

It is necessary for the gas sensor according to the first embodiment that the first and second inner pumping electrodes 26, 40 and the first and second measuring electrodes 34, 48 arranged in the first internal space 20 and the second internal space 22 do not cause reduction or decomposition of the measurement gas component (NOx) in the respective atmospheres at the ambient temperatures and at the controlled partial pressures of oxygen in the respective internal spaces 20, 22. Accordingly, an electrode metal such as Au and Ni having no or low reducing or decomposing ability for the measurement gas component is used for the first and second inner pumping electrodes 26, 40 and the first and second measuring electrodes 34, 48. It is advantageous to use a cermet electrode composed of the metal as described above, and a cermet electrode based on the use of an alloy obtained by adding a metal such as Au and Ni having no catalytic property to a noble metal such as Pt, Pd, and Rh.

The third inner pumping electrode 54 arranged in the third internal space 24 is desirably composed of a cermet electrode of Rh, Pt or the like capable of reducing or decomposing the measurement gas component (NOx) in the atmosphere at the environmental temperature and at the partial pressure of oxygen in the third internal space 24.

It is a matter of course to use, as the third inner pumping electrode 54, those obtained by stacking and arranging, on an ordinary electrode, an Rh or Pt electrode or a catalyst comprising a NOx-reducing metal carried on a ceramic porous material such as alumina, and those obtained by arranging an Rh catalyst electrode on a Pt electrode.

As described above, the respective electrodes provided in the gas sensor according to the first embodiment, especially the inner pumping electrode and the measuring electrode arranged in the internal space are desirably composed of a cermet comprising an electrode metal and an appropriate ceramic. When the third inner pumping electrode which also serves as a NOx-reducing catalyst is used, it is desirably composed of a porous cermet electrode comprising a ceramic and a metal such as Rh and Pt capable of reducing NOx.

The NOx-reducing catalyst may be provided adjacent to the third inner pumping electrode 54 of the third electrochemical pumping cell 58 for pumping out oxygen in the third internal space 24. Alternatively, a NOx-reducing catalyst layer may be formed on the electrode by stacking, for example, porous alumina carrying a NOx-reducing catalyst composed of Rh or the like on the third inner pumping electrode 54 by means of printing or the like.

Figure 4:
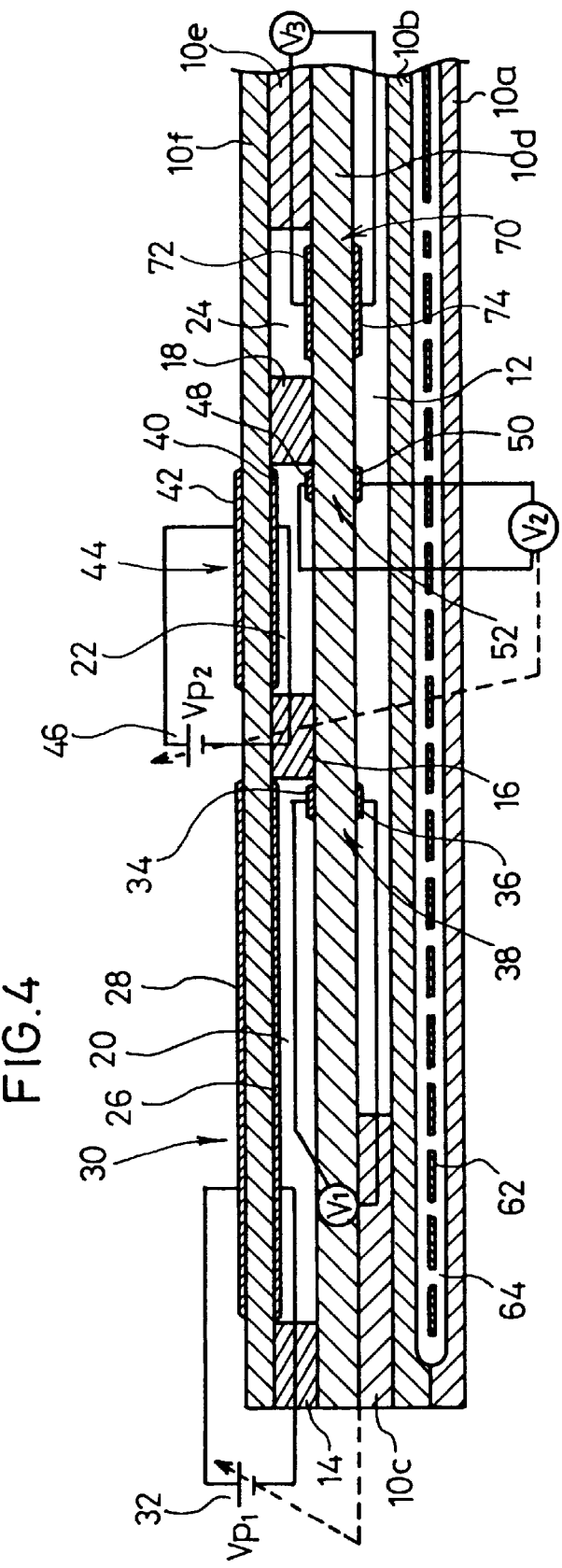
FIG. 4 shows a schematic cross-sectional view illustrating an arrangement of a modified embodiment of the gas sensor according to the first embodiment.

Next, a modified embodiment of the gas sensor according to the first embodiment will be explained with reference to FIG. 4. Components or parts corresponding to those shown in FIG. 1 are designated by the same reference numerals, duplicate explanation of which will be omitted.

The gas sensor according to the modified embodiment is constructed in approximately the same manner as the gas sensor according to the first embodiment. However, the former is different from the latter in that a third electrochemical sensor cell 70 is provided, in place of the third electrochemical pumping cell 58.

The third electrochemical sensor cell 70 comprises a third measuring electrode 72 formed on a portion of the upper surface of the first solid electrolyte layer 10d for forming the third internal space 24, a third reference electrode 74 formed on a portion of the lower surface of the first solid electrolyte layer 10d, the portion being exposed to the reference gas-introducing space 12 and corresponding to the third measuring electrode 72, and the first solid electrolyte layer 10d.

In this modified embodiment, an electromotive force, which corresponds to a difference in oxygen concentration between the atmosphere around the third measuring electrode 72 and the atmosphere around the third reference electrode 74, is generated between the third measuring electrode 72 and the third reference electrode 74 of the third electrochemical sensor cell 70.

Therefore, when the electromotive force generated between the respective electrodes 72, 74 is measured by using a voltmeter V3, the partial pressure of oxygen in the atmosphere around the third measuring electrode 72, in other words, the partial pressure of oxygen defined by oxygen produced by reduction or decomposition of the measurement gas component (NOx) is detected as a voltage value.

It is assumed that the NO concentration of NOx as the measurement gas component is 0 ppm. When the oxygen concentration in the atmosphere in the first internal space 20 is controlled to be a value ($10^{-7}$ atm) corresponding to a pumping voltage of 300 mV in the first electrochemical pumping cell 30, if oxygen in the atmosphere in the third internal space 24 is not subjected to pumping, then the oxygen concentration in the atmosphere in the third internal space 24 is also $10^{-7}$ atm, and the electromotive force between the third measuring electrode 72 and the third reference electrode 74 is 300 mV.

For example, it is assumed that NO is present at 10 ppm in the measurement gas. The third measuring electrode 72 also functions as a NOx-reducing catalyst in the same manner as the third inner pumping electrode 54 of the third electrochemical pumping cell 58 described above (see FIG. 1). Accordingly, the NO-reducing or decomposing reaction is caused on the third measuring electrode 72, and the oxygen concentration in the atmosphere around the third measuring electrode 72 is increased. Thus the electromotive force, which is generated between the third measuring electrode 72 and the third reference electrode 74, is decreased. The degree of the decrease in electromotive force represents the NO concentration.

Namely, the electromotive force, which is outputted from the third electrochemical sensor cell 70 constructed by the third measuring electrode 72, the third reference electrode 74, and the first solid electrolyte layer 10d, represents the NO concentration in the measurement gas.

Figure 5:
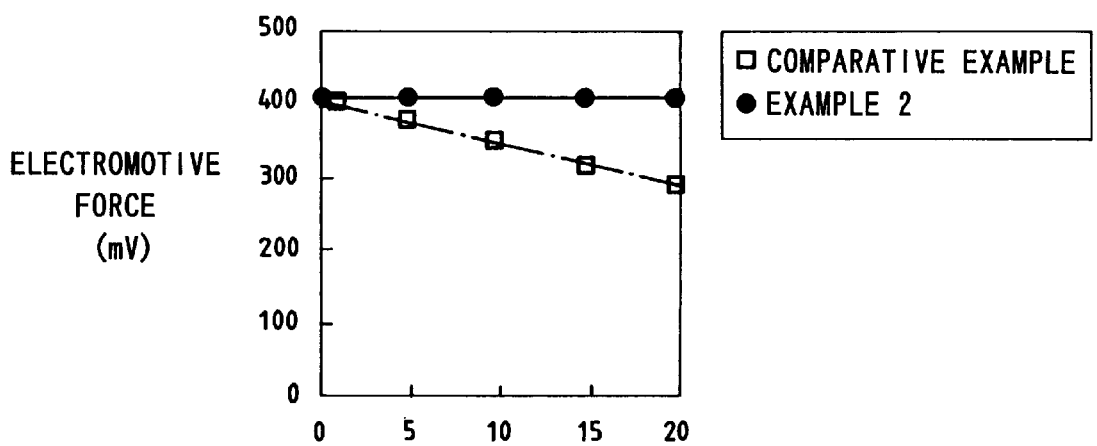
FIG. 5 shows characteristic curves illustrating the change in electromotive force generated from a third electrochemical sensor cell, obtained when the oxygen concentration in a measurement gas was changed in a range of 0 to 20%, wherein a solid line represents the characteristic obtained in Example 2, and a chain line represents the characteristic obtained in Comparative Example.

In FIG. 5, there were prepared Example 2 concerning a gas sensor constructed in the same manner as the gas sensor according to the modified embodiment, and Comparative Example concerning a gas sensor constructed without providing the second internal space 22, the second electrochemical pumping cell 44, and the second electrochemical sensor cell 52. FIG. 5 shows the change in the electromotive force generated from the third electrochemical sensor cell 70, obtained when basic gas components were based on an $N_2$—$O_2$—$H_2O$ system, and the oxygen concentration in the measurement gas was changed in a range of 0 to 20%. The NO component was not contained in the measurement gas in order to accurately measure the way of change in electromotive force when only the oxygen concentration in the measurement gas was changed.

In FIG. 5, a characteristic curve obtained in Example 2 is represented by a solid line, and a characteristic curve obtained in Comparative Example is represented by a chain line. In Example 2, the first electrochemical pumping cell 30 had a pumping voltage of 300 mV, and the second electrochemical pumping cell 44 had a pumping voltage of 430 mV. In Comparative Example, the first electrochemical pumping cell 30 had a pumping voltage of 430 mV.

As clarified from the result shown in FIG. 5, the electromotive force was decreased in Comparative Example as the oxygen concentration in the measurement gas was increased. For example, when the oxygen concentration was 0%, the electromotive force was 430 mV. When the oxygen concentration was 20%, the electromotive force was 280 mV, exhibiting a large change of 150 mV. Accordingly, it is understood that it is difficult in Comparative Example to accurately determine the NO concentration from the electromotive force of the third electrochemical sensor cell 70.

On the contrary, in Example 2, even when the oxygen concentration in the measurement gas was changed in a range of 0 to 20%, the electromotive force generated from the third electrochemical sensor cell 70 was scarcely changed, owing to the pumping action effected by the second electrochemical pumping cell 44. Accordingly, when the NO component is contained in the measurement gas, the electromotive force corresponding to the amount of NO is generated between the third measuring electrode 72 and the third reference electrode 74 for constructing the third electrochemical sensor cell 70. An accurate amount of NO can be determined by detecting the generated electromotive force.

Next, a gas sensor according to a second embodiment will be explained with reference to FIGS. 6 and 7. Components or parts corresponding to those shown in FIG. 1 are designated by the same reference numerals, duplicate explanation of which will be omitted.

Figure 6:
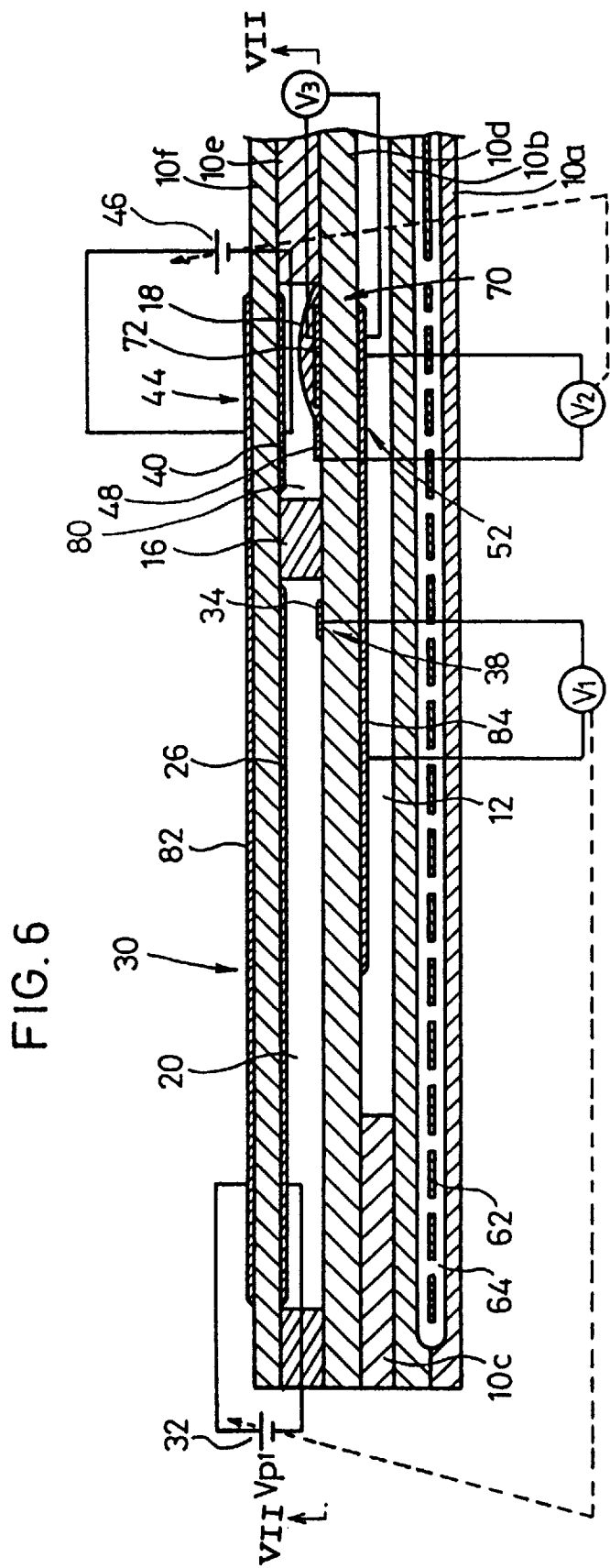
FIG. 6 shows a schematic cross-sectional view illustrating an arrangement of a gas sensor according to a second embodiment.

As shown in FIG. 6, the gas sensor according to the second embodiment is constructed in approximately the same manner as the modified embodiment of the gas sensor according to the first embodiment. However, the former is different from the latter in that the second internal space 22 and the third internal space 24 are integrated into one combined internal space 80 composed of a flat space having an approximately rectangular planar configuration. Namely, the combined internal space 80 is comparted and formed by the lower surface of the second solid electrolyte layer 10f, the side surface of the second diffusion rate-determining section 16, side surfaces of the second spacer layer 10e, and the upper surface of the first solid electrolyte layer 10d.

A second inner pumping electrode 40 having an approximately rectangular planar configuration and composed of a porous cermet electrode is formed on an entire surface portion of the lower surface of the second solid electrolyte layer 10f for forming the combined internal space 80. A second measuring electrode 48 having an approximately rectangular planar configuration and composed of a porous cermet electrode is formed on a portion of the upper surface of the first solid electrolyte layer 10d for forming the combined internal space 80, the portion being separated from the second diffusion rate-determining section 16.

A third measuring electrode 72 having an approximately rectangular planar configuration and composed of a porous cermet electrode is formed on a portion of the upper surface of the first solid electrolyte layer 10d for forming the combined internal space 80, the second measuring electrode 48 being not formed on the portion. An alumina film for constructing a third diffusion rate-determining section 18 is formed so that the third measuring electrode 72 is covered therewith.

In the gas sensor according to the second embodiment, an outer pumping electrode 82, which commonly serves as the first outer pumping electrode 28 and the second outer pumping electrode 42 (see FIG. 1), is formed on a continuous portion of the upper surface of the second solid electrolyte layer 10f, the portion ranging from the first internal space 20 to the combined internal space 80. A common reference electrode 84, which commonly serves as the first reference electrode 36, the second reference electrode 50, and the third reference electrode 74 (see FIG. 4), is formed on a continuous portion of the lower surface of the first solid electrolyte layer 10d, the portion being exposed to the reference gas-introducing space 12 and ranging from the first internal space 20 to the combined internal space 80.

Namely, in the gas sensor according to the second embodiment, a first electrochemical pumping cell 30 is constructed by the outer pumping electrode 82 formed on the upper surface of the second solid electrolyte layer 10f, the first inner pumping electrode 26 formed in the first internal space 20, and the second solid electrolyte layer 10f. A first electrochemical sensor cell 38 is constructed by the common reference electrode 84 formed on the lower surface of the first solid electrolyte layer 10d, the first measuring electrode 34 formed in the first internal space 20, and the first solid electrolyte layer 10d. A second electrochemical pumping cell 44 is constructed by the outer pumping electrode 82 formed on the upper surface of the second solid electrolyte layer 10f, the second inner pumping electrode 40 formed in the combined internal space 80, and the second solid electrolyte layer 10f. A second electrochemical sensor cell 52 is constructed by the common reference electrode 84 formed on the lower surface of the first solid electrolyte layer 10d, the second measuring electrode 48 formed in the combined internal space 80, and the first solid electrolyte layer 10d. A third electrochemical sensor cell 70 is constructed by the common reference electrode 84 formed on the lower surface of the first solid electrolyte layer 10d, the third measuring electrode 72 formed in the combined internal space 80, and the first solid electrolyte layer 10d.

Figure 7:
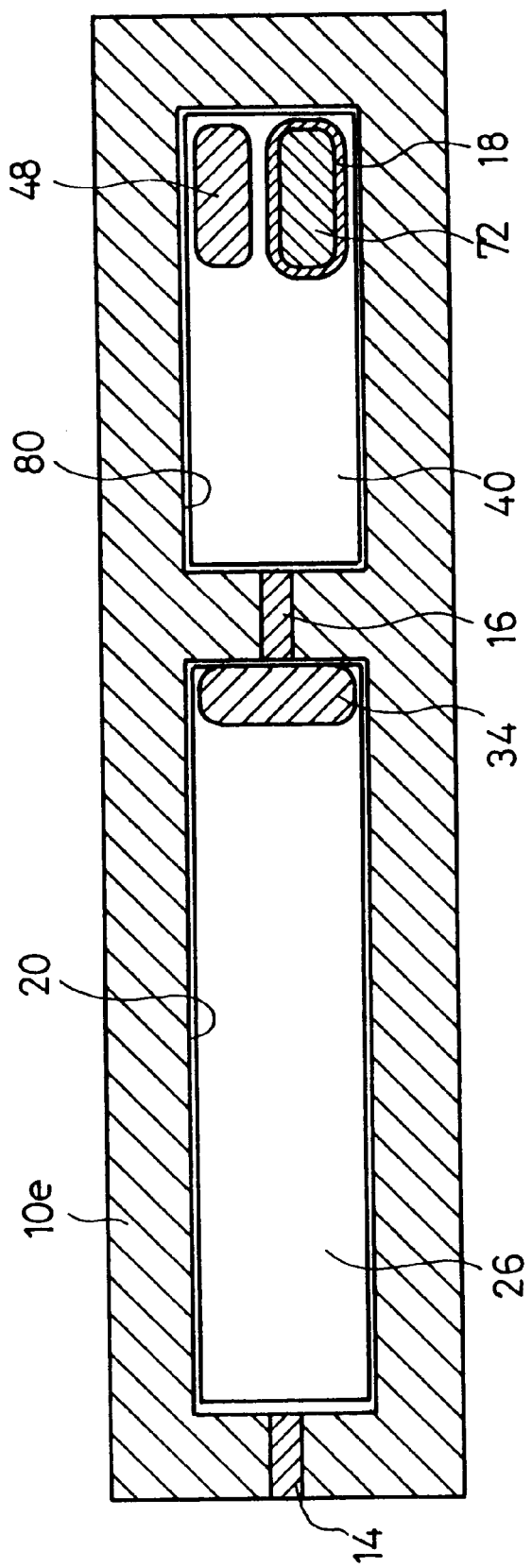
FIG. 7 shows a cross-sectional view taken along a line VII—VII in FIG. 6.

Especially, as shown in FIG. 7, the gas sensor according to the second embodiment is constructed as follows. Namely, the second measuring electrode 48 and the third measuring electrode 72 are arranged in parallel to one another in the combined internal space 80. The second measuring electrode 48 and the third measuring electrode 72 are arranged at positions adjacent to each other.

Next, the operation of the gas sensor according to the second embodiment will be explained. At first, the measurement gas existing in the external space is introduced into the first internal space 20 under a predetermined diffusion resistance via the first diffusion rate-determining section 14. The measurement gas introduced into the first internal space 20 is adjusted to have a predetermined oxygen concentration by the aid of the pumping action effected by the first electrochemical pumping cell 30.

The gas, which has been adjusted to have the predetermined oxygen concentration by the aid of the first electrochemical pumping cell 30, is introduced into the combined internal space 80 under a predetermined diffusion resistance via the second diffusion rate-determining section 16. The gas introduced into the combined internal space 80 is finely adjusted to have a predetermined oxygen concentration by the aid of the pumping action effected by the second electrochemical pumping cell 44.

The gas, which has been finely adjusted to have the predetermined oxygen concentration by the aid of the second electrochemical pumping cell 44, is introduced into the third electrochemical pumping cell 58 under a predetermined diffusion resistance via the third diffusion rate-determining section 18 in the same combined internal space 80.

In this embodiment, an electromotive force, which corresponds to a difference in oxygen concentration between the atmosphere around the third measuring electrode 72 and the atmosphere around the common reference electrode 84, is generated between the third measuring electrode 72 and the common reference electrode 84 of the third electrochemical sensor cell 70.

Therefore, the partial pressure of oxygen in the atmosphere around the third measuring electrode 72, in other words, the partial pressure of oxygen defined by oxygen generated by the reduction or decomposition of the measurement gas component (NOx) is detected as a voltage value by measuring the electromotive force generated between the respective electrodes 72, 84 by using a voltmeter V3.

This embodiment also makes it possible to avoid interference exerted by the change in oxygen concentration in exhaust gas on the detecting sensitivity for the amount of the objective gas component existing in the measurement gas, and improve the measurement accuracy for the measurement gas component, in the same manner as described in the modified embodiment of the gas sensor according to the first embodiment.

Especially, as shown in FIG. 7, the gas sensor according to the second embodiment is constructed as follows. Namely, the second measuring electrode 48 and the third measuring electrode 72, which are formed in the combined internal space 80, are arranged in parallel to one another, and the second measuring electrode 48 and the third measuring electrode 72 are disposed adjacent to one another. Accordingly, the oxygen concentration in the vicinity of the second measuring electrode 48 can be more accurately controlled. Even when the third electrochemical sensor cell 70 is provided in the combined internal space 80, it is possible to accurately measure the amount of the objective component existing in the measurement gas.

It is unnecessary for the gas sensor according to the second embodiment to provide a new internal space (the third internal space 24 concerning the first embodiment, see FIG. 1) for disposing the third electrochemical sensor cell 70. Therefore, it is possible to facilitate miniaturization of the entire structure of the gas sensor.

In the gas sensor according to the second embodiment, the first outer pumping electrode 28 and the second outer pumping electrode 42 of the gas sensor according to the first embodiment are replaced with one common member of the outer pumping electrode 82. Further, the first reference electrode 36, the second reference electrode 50, and the third reference electrode 74 of the gas sensor according to the first embodiment are replaced with one common member of the common reference electrode 84. Therefore, it is possible to decrease the number of terminals led to the outside, as compared with the gas sensor according to the first embodiment. Thus it is possible to simplify the wiring steps and simplify the circuit layout for the peripheral circuits.

In the gas sensor according to the second embodiment, the third diffusion rate-determining section 18 can be omitted by appropriately adjusting the relational arrangement of the second inner pumping electrode 40 and the third measuring electrode 72 in the combined internal space 80. In such an arrangement, it is unnecessary to form the third diffusion rate-determining section 18 so that the third measuring electrode 72 is surrounded. Accordingly, it is possible to simplify the production steps.

Next, a gas sensor according to a third embodiment will be explained with reference to FIGS. 8 and 9. Components or parts corresponding to those shown in FIGS. 6 and 7 are designated by the same reference numerals, duplicate explanation of which will be omitted.

Figure 8:
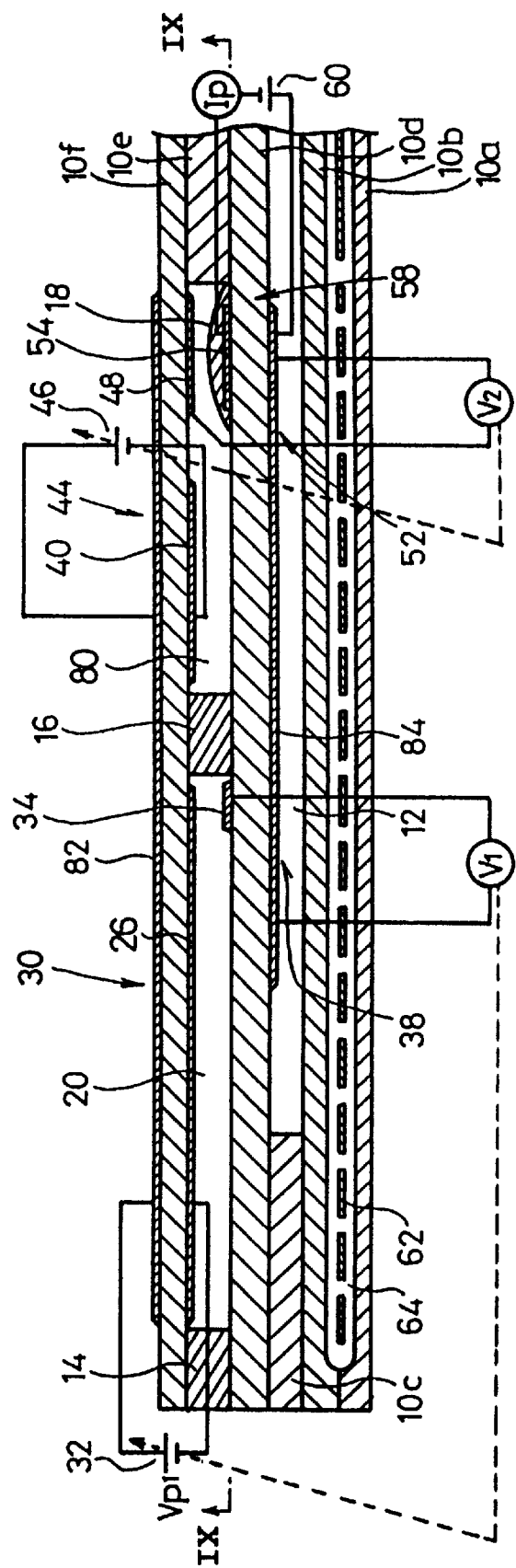
FIG. 8 shows a schematic cross-sectional view illustrating an arrangement of a gas sensor according to a third embodiment.
Figure 9:
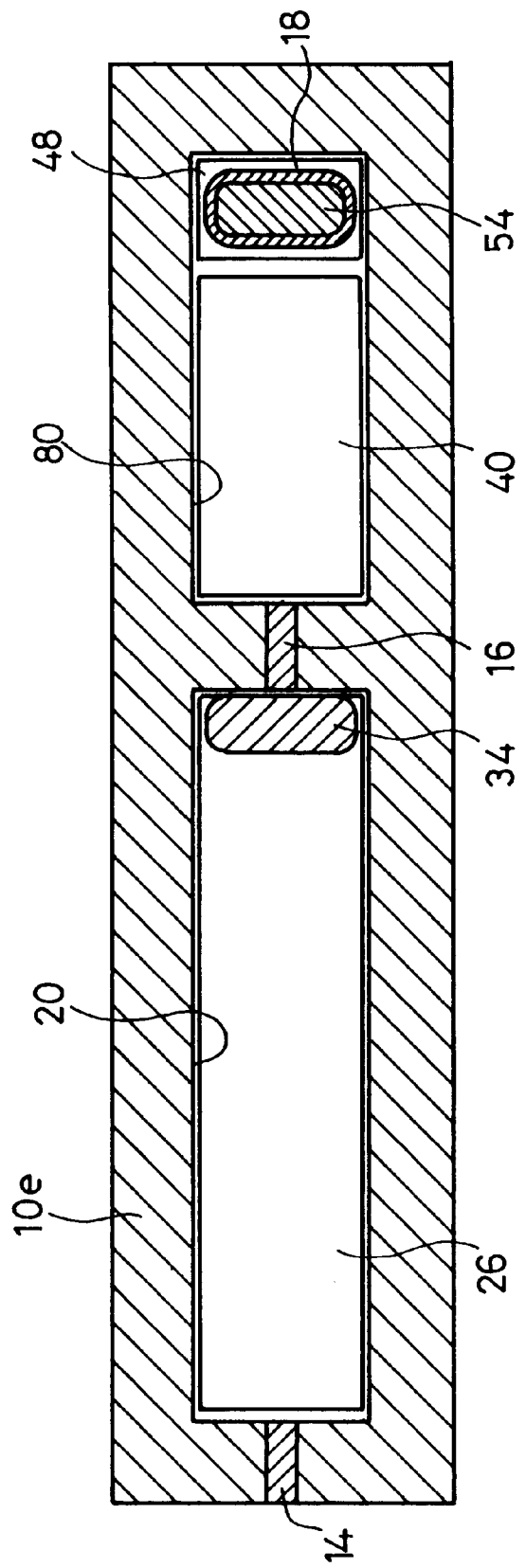
FIG. 9 shows a cross-sectional view taken along a line IV—IV in FIG. 8.

As shown in FIGS. 8 and 9, the gas sensor according to the third embodiment is constructed in approximately the same manner as the gas sensor according to the second embodiment. However, the former is different from the latter in that a third electrochemical pumping cell 58 is provided in place of the third electrochemical sensor cell 70.

Specifically, a second measuring electrode 48 of the second electrochemical sensor cell 52 is formed on a portion of the lower surface of the second solid electrolyte layer 10f for forming the combined internal space 80, the portion being separated from the second diffusion rate-determining section 16. A third inner pumping electrode 54 of the third electrochemical pumping cell 58 is formed at a position on the upper surface of the first solid electrolyte layer 10d for forming the combined internal space 80, the position being opposed to the second measuring electrode 48.

The operation of the gas sensor according to the third embodiment will be briefly explained. The third electrochemical pumping cell 58 is operated so that the component having bound oxygen in the introduced measurement gas is reduced or decomposed, and oxygen produced by the reduction or decomposition is pumped out.

A pumping current, which is allowed to flow in accordance with the pumping operation (pumping out of oxygen) effected by the third electrochemical pumping cell 58, is detected by an ammeter Ip to obtain a current value. The amount of the specified component in the measurement gas is determined on the basis of the current value.

When the oxygen concentration in the measurement gas is greatly changed (in a range of 0 to 20%) during the period in which the foregoing operation is performed, then the distribution of oxygen concentration in the measurement gas introduced into the first internal space 20 is greatly changed, and the amount of oxygen introduced into the combined internal space 80 is also changed.

The concentration of oxygen introduced into the combined internal space 80 is finely adjusted by the second electrochemical pumping cell 44. However, owing to the pumping operation effected by the first electrochemical pumping cell 30 in the first internal space 20, the change in concentration of oxygen introduced into the combined internal space 80 is greatly reduced as compared with the change in concentration of oxygen in the measurement gas (the measurement gas introduced into the first internal space 20). Accordingly, it is possible to accurately control the oxygen concentration in the combined internal space 80 to be constant.

In this embodiment, the pumping operation effected by the second electrochemical pumping cell 44 is subjected to feedback control on the basis of the second electrochemical sensor cell 52 in the combined internal space 80. Therefore, it is possible to more accurately control the oxygen concentration in the combined internal space 80.

As described above, the oxygen concentration is accurately controlled to be constant in the combined internal space 80. Therefore, the concentration of oxygen introduced into the third electrochemical pumping cell 58 is scarcely affected by the change in oxygen concentration in the measurement gas (the measurement gas introduced into the first internal space 20). As a result, the pumping current value, which is detected by the ammeter Ip in accordance with the pumping out for oxygen effected by the third electrochemical pumping cell 58, is not affected by the change in oxygen concentration in the measurement gas. The pumping current value is a value which accurately corresponds to the amount of the objective component existing in the measurement gas.

Namely, the gas sensor according to the third embodiment makes it possible to avoid interference exerted by the change in oxygen concentration in exhaust gas on the detecting sensitivity for the amount of the objective component existing in the measurement gas, and improve the measurement accuracy for the measurement gas component.

It is unnecessary to provide a new internal space (the third internal space 24 in the first embodiment) for providing the third electrochemical pumping cell 58. Therefore, it is possible to facilitate miniaturization of the entire structure of the gas sensor. Further, the first outer pumping electrode 28 and the second outer pumping electrode 42 of the gas sensor according to the first embodiment are replaced with one common member of the outer pumping electrode 82. Moreover, the first reference electrode 36, the second reference electrode 50, and the third outer pumping electrode 56 of the gas sensor according to the first embodiment are replaced with one common member of the common reference electrode 84. Therefore, it is possible to decrease the number of terminals led to the outside, as compared with the gas sensor according to the first embodiment. Thus it is possible to simplify the wiring steps and simplify the circuit layout for the peripheral circuits.

Especially, in the gas sensor according to the third embodiment, the second measuring electrode 48 and the third inner pumping electrode 54 are arranged opposingly to one another in the combined internal space 80. Thus the relational arrangement is given in which the second measuring electrode 48 is scarcely affected by the third inner pumping electrode 54 when the concentration of the measurement gas component is measured on the basis of the pumping current. Accordingly, even when the third electrochemical pumping cell 58 is provided in the combined internal space 80, the amount of the objective component existing in the measurement gas can be accurately measured.

Figure 10:
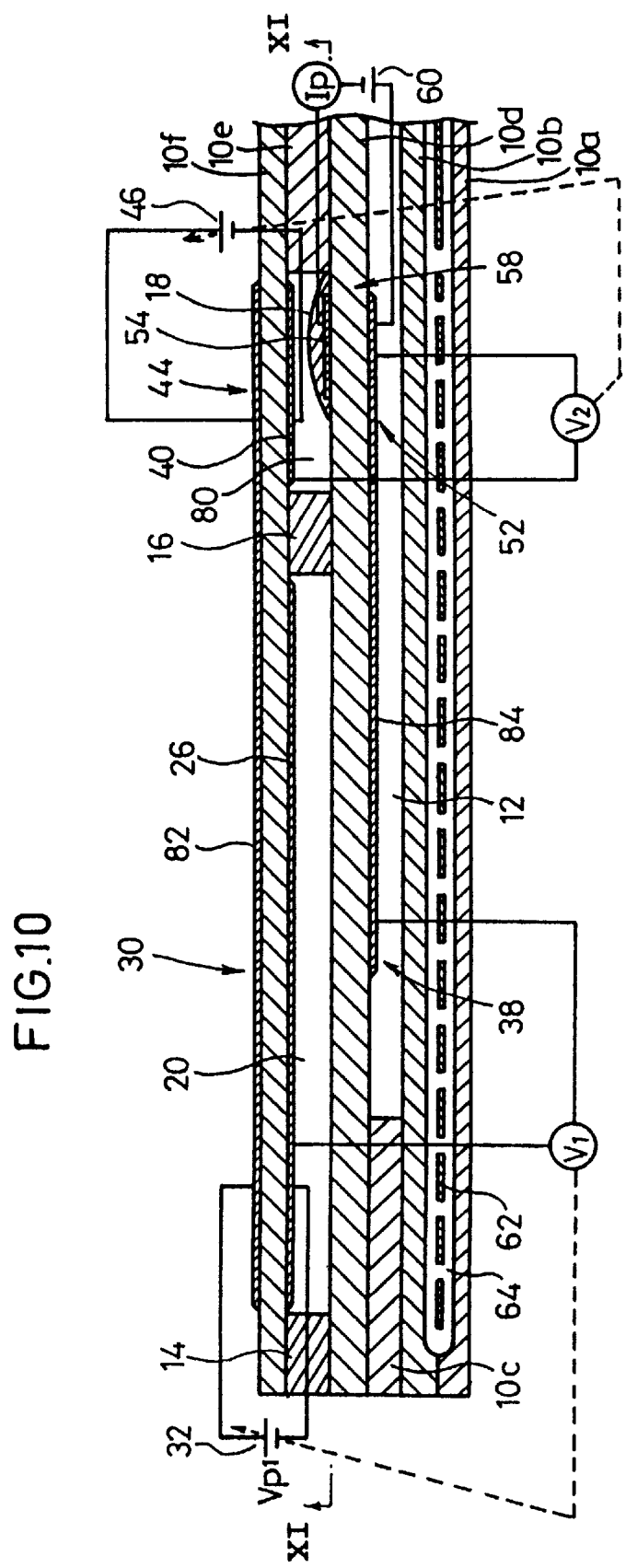
FIG. 10 shows a schematic cross-sectional view illustrating an arrangement of a gas sensor according to a fourth embodiment.

Next, a gas sensor according to a fourth embodiment will be explained with reference to FIGS. 10 and 11. Components or parts corresponding to those shown in FIGS. 6 and 7 are designated by the same reference numerals, duplicate explanation of which will be omitted.

The gas sensor according to the fourth embodiment is constructed in approximately the same manner as the gas sensor according to the third embodiment. However, the former is different from the latter in that the first inner pumping electrode 26 of the first electrochemical pumping cell 30 also serves as the first measuring electrode 34 (see FIG. 8) of the first electrochemical sensor cell 38, and that the second inner pumping electrode 40 of the second electrochemical pumping cell 44 also serves as the second measuring electrode 48 (see FIG. 8) of the second electrochemical sensor cell 52.

Specifically, the gas sensor according to the fourth embodiment is constructed as follows. Namely, a variable power source 32 is connected between an outer pumping electrode 82 formed on the upper surface of the second solid electrolyte layer 10f and a first inner pumping electrode 26 formed on an entire surface portion of the lower surface of the second solid electrolyte layer 10f for forming the first internal space 20. A voltmeter V1 is connected between the first inner pumping electrode 26 and a common reference electrode 84 formed on the lower surface of the first solid electrolyte layer 10d. A variable power source 46 is connected between the outer pumping electrode 82 and a second inner pumping electrode 40 formed on an entire surface portion of the lower surface of the second solid electrolyte layer 10f for forming the combined internal space 80. A voltmeter V2 is connected between the second inner pumping electrode 40 and the common reference electrode 84.

The operation of the gas sensor according to the fourth embodiment will be explained. At first, the measurement gas is introduced into the first internal space 20. In this state, the voltmeter V1 measures a terminal voltage between the first inner pumping electrode 26 of the first electrochemical pumping cell 30 and the common reference electrode 84 formed on the side of the reference gas-introducing space 12. The variable power source 32 is subjected to feedback control on the basis of the measured voltage. Accordingly, the pumping operation effected by the first electrochemical pumping cell 30 is controlled so that the partial pressure of oxygen in the atmosphere in the first internal space 20 has a predetermined value which is sufficiently low to control the partial pressure of oxygen in the next combined internal space 80.

In this embodiment, the measured voltage detected by the voltmeter V1 provided for the first electrochemical sensor cell 38 is the terminal voltage between the first inner pumping electrode 26 of the first electrochemical pumping cell 30 and the common reference electrode 84 disposed in the reference gas-introducing space 12. Accordingly, when the amount of oxygen pumped out by the first electrochemical pumping cell 30 is changed, and the oxygen concentration in the atmosphere in the first internal space 20 is changed, then the terminal voltage between the first inner pumping electrode 26 of the first electrochemical pumping cell 30 and the common reference electrode 84 is changed without any time delay. Therefore, no oscillation phenomenon occurs in the feedback control system for the variable power source 32, and it is possible to highly accurately control the oxygen concentration in the first internal space 20.

Such an advantage is also obtained in the feedback control for the variable power source 46 provided for the second electrochemical pumping cell 44. The voltmeter V2 measures the terminal voltage between the second inner pumping electrode 40 of the second electrochemical pumping cell 44 and the common reference electrode 84 formed on the side of the reference gas-introducing space 12. The variable power source 46 is subjected to feedback control on the basis of the measured voltage. Accordingly, the pumping operation effected by the second electrochemical pumping cell 44 is controlled so that the partial pressure of oxygen in the atmosphere in the combined internal space 80 has a low value of the partial pressure of oxygen at which the measurement for the amount of the objective component is not substantially affected, under the condition in which the measurement gas component (NOx) is not substantially reduced or decomposed.

In this embodiment, the measured voltage detected by the voltmeter V2 for the second electrochemical sensor cell 52 is the terminal voltage between the second inner pumping electrode 40 of the second electrochemical pumping cell 44 and the common reference electrode 84 disposed in the reference gas-introducing space. Accordingly, when the amount of oxygen pumped out by the second electrochemical pumping cell 44 is changed, and the oxygen concentration in the atmosphere in the combined internal space 80 is changed, then the terminal voltage between the second inner pumping electrode 40 of the second electrochemical pumping cell 44 and the common reference electrode 84 is changed without any time delay. Therefore, no oscillation phenomenon occurs in the feedback control system for the variable power source 46, and it is possible to highly accurately control the oxygen concentration in the combined internal space 80.

In the gas sensor according to the fourth embodiment, it is possible to avoid interference exerted by the change in concentration of oxygen in exhaust gas on the detecting sensitivity for the amount of the objective component existing in the measurement gas, and improve the measurement accuracy for the measurement gas component, in the same manner as the gas sensor according to the third embodiment. Further, it is possible to facilitate miniaturization of the entire structure of the gas sensor, and it is possible to simplify the wiring steps and simplify the circuit layout for the peripheral circuits.

Especially, in the gas sensor according to the fourth embodiment, it is unnecessary to provide a wide area for forming the electrode in the first internal space 20 and the combined internal space 80. Therefore, the structure of the gas sensor itself can be miniaturized. When the gas sensor is designed to have an identical size, it is possible to provide a large volume for the first internal space 20. Accordingly, the pumping function effected by the first electrochemical pumping cell 30 can be enhanced, and it is possible to finely adjust the oxygen concentration in the combined internal space 80 with a higher degree of accuracy.

The first inner pumping electrode 26 and the first measuring electrode 34 (see FIG. 8) are provided as the common electrode, and the second inner pumping electrode 40 and the second measuring electrode 48 (see FIG. 8) are provided as the common electrode. Accordingly, for example, when the amount of oxygen pumped out by the first electrochemical pumping cell 30 provided for the first internal space 20 is changed, and the oxygen concentration in the first internal space 20 is changed, then the measured voltage obtained by the first electrochemical sensor cell 38 is also changed without any time delay. Therefore, it is possible to appropriately perform, without any oscillation, the feedback control for the first electrochemical pumping cell 30, effected by the first electrochemical sensor cell 38. Such an advantage is also obtained in the feedback control effected by the second electrochemical sensor cell 52 for the second electrochemical pumping cell 44 in the combined internal space 80.

The objective measurement gas component is NOx in the case of the gas sensors according to the first to fourth embodiments described above. However, the present invention can be also effectively applied to the measurement for bound oxygen-containing gas components other than NOx, such as $H_2O$ and $CO_2$, which may be affected by oxygen existing in the measurement gas.

It is a matter of course that this invention is not limited to the embodiments described above, which can be constructed in other various forms without deviating from the gist or essential characteristics of this invention.

What is claimed is:

1. A gas sensor for determining an amount of a specified component in a measurement gas by reducing or decomposing said component having bound oxygen in said measurement gas and measuring an amount of oxygen produced during said reduction or decomposition, said gas sensor comprising:

first and second substrates comprising solid electrolytes stacked through a spacer thereby defining at least two internal spaces between said electrolytes;

a first diffusion rate-determining section for introducing said measurement gas under a predetermined diffusion resistance;

a first internal space for making communication with an atmosphere of said measurement gas via said first diffusion rate-determining section;

a first electrochemical pumping cell comprising said first solid electrolyte for constructing said first internal space and a pair of first pumping electrodes provided in contact therewith;

a first electrochemical sensor cell comprising said second solid electrolyte for constructing said first internal space and a pair of first measuring electrodes provided in contact therewith;

a second diffusion rate-determining section for introducing, under a predetermined diffusion resistance, said gas adjusted to have a predetermined value of oxygen concentration in said first internal space;

a second internal space for making communication with said atmosphere of said measurement gas via said second diffusion rate-determining section;

a second electrochemical pumping cell comprising said first solid electrolyte for constructing said second internal space and a pair of second pumping electrodes provided in contact therewith;

a second electrochemical sensor cell comprising said second solid electrolyte for constructing said second internal space and a pair of second measuring electrodes with one of said second measuring electrodes provided in contact therewith and with another of said second measuring electrodes in contact with said first solid electrolyte;

a third diffusion rate-determining section for introducing, under a predetermined diffusion resistance, said gas adjusted to have a predetermined value of oxygen concentration in said second internal space;

a third electrochemical pumping cell having two pumping electrodes for pumping out oxygen produced by reduction or decomposition of said component having bound oxygen in said measurement gas introduced via said third diffusion rate-determining section; and a current-detecting means for detecting a pumping current which is allowed to flow in accordance with operation of said third electrochemical pumping cell, wherein said another of said second measuring electrodes and one of said third electrochemical pumping electrodes are provided in said second internal space, and are arranged opposingly to one another across said second internal space.

2. The gas sensor according to claim 1, wherein said third electrochemical pumping cell comprises said second solid electrolyte for constructing said second internal space and said pumping electrodes of the third electrochemical pumping cell are provided in contact therewith.

3. The gas sensor according to claim 2, wherein one of said second pumping electrodes and one of said second measuring electrodes are provided in said second internal space as a single common electrode.

4. The gas sensor according to claim 1, wherein one of said first pumping electrodes and one of said first measuring electrodes are disposed in said first internal space and one of said second pumping electrodes and one of said second measuring electrodes are disposed in said second internal space, all four of said electrodes disposed in said first and second internal spaces comprising a material having no or low reducing ability for NO in said measurement gas.

5. The gas sensor according to claim 4, wherein a cermet of Au and ZrO2, or a cermet of Au, an alloy of Pt group element, and ZrO2, is used as said material having no or low reducing ability for NO in said measurement gas.

6. A gas sensor for determining an amount of a specified component in a measurement gas by reducing or decomposing said component having bound oxygen in said measurement gas and measuring an amount of oxygen produced during said reduction or decomposition, said gas sensor comprising:

first and second substrates comprising solid electrolytes stacked through a spacer thereby defining at least two internal spaces between said electrolytes;

a first diffusion rate-determining section for introducing said measurement gas under a predetermined diffusion resistance;

a first internal space for making communication with an atmosphere of said measurement gas via said first diffusion rate-determining section;

a first electrochemical pumping cell comprising said solid first electrolyte for constructing said first internal space and a pair of first pumping electrodes provided in contact therewith;

a first electrochemical sensor cell comprising said second solid electrolyte for constructing said first internal space and a pair of first measuring electrodes provided in contact therewith;

a second diffusion rate-determining section for introducing, under a predetermined diffusion resistance, said gas adjusted to have a predetermined value of oxygen concentration in said first internal space;

a second internal space for making communication with said atmosphere of said measurement gas via said second diffusion rate-determining section;

a second electrochemical pumping cell comprising said first solid electrolyte for constructing said second internal space and a pair of second pumping electrodes provided in contact therewith;

a second electrochemical sensor cell comprising said second solid electrolyte for constructing said second internal space and a pair of second measuring electrodes provided in contact therewith;

a third diffusion rate-determining section for introducing, under a predetermined diffusion resistance, said gas adjusted to have a predetermined value of oxygen concentration in said second internal space;

a third electrochemical sensor cell having two measuring electrodes for outputting an electromotive force corresponding to a partial pressure of oxygen defined by oxygen produced by reduction or decomposition of said component having bound oxygen in said measurement gas introduced via said third diffusion rate-determining section; and a voltage-detecting means for detecting said electromotive force outputted from said third electrochemical sensor cell, wherein one of said second measuring electrodes and one of said third electrochemical measuring electrodes are provided in said second internal space, and are arranged in parallel across said second internal space.

7. The gas sensor according to claim 6, wherein said third electrochemical sensor cell comprises said second solid electrolyte for constructing said second internal space and said measuring electrodes of the third electrochemical sensor cell are provided in contact therewith.

8. The gas sensor according to claim 7, wherein one of said second pumping electrodes and one of said second measuring electrodes are provided in said second internal space as a single common electrode.

9. The gas sensor according to claim 6, wherein one of said first pumping electrodes and one of said first measuring electrodes are disposed in said first internal space and one of said second pumping electrodes and one of said second measuring electrodes are disposed in said second internal space, all four of said electrodes disposed in said first and second internal spaces comprising a material having no or low reducing ability for NO in said measurement gas.

10. The gas sensor according to claim 9, wherein a cermet of Au and $ZrO_2$, or a cermet of Au, an alloy of Pt group element, and $ZrO_2$, is used as said material having no or low reducing ability for NO in said measurement gas.

* * * * *